United States Patent
Sun

(10) Patent No.: US 11,419,842 B2
(45) Date of Patent: *Aug. 23, 2022

(54) NEUTRAL PH COMPOSITIONS OF DOCETAXEL AND HUMAN SERUM ALBUMIN

(71) Applicant: Zhuhai Beihai Biotech Co., Ltd., Zhuhai (CN)

(72) Inventor: Qun Sun, Princeton, NJ (US)

(73) Assignee: Zhuhai Beihai Biotech Co., Ltd., Zhuhai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/345,615

(22) PCT Filed: Oct. 27, 2017

(86) PCT No.: PCT/US2017/058697
§ 371 (c)(1),
(2) Date: Apr. 26, 2019

(87) PCT Pub. No.: WO2018/081520
PCT Pub. Date: May 3, 2018

(65) Prior Publication Data
US 2019/0336467 A1   Nov. 7, 2019

Related U.S. Application Data

(60) Provisional application No. 62/413,603, filed on Oct. 27, 2016, provisional application No. 62/420,397, filed on Nov. 10, 2016.

(51) Int. Cl.
| | |
|---|---|
| *A61K 31/337* | (2006.01) |
| *A61K 47/64* | (2017.01) |
| *A61K 9/08* | (2006.01) |
| *A61K 47/42* | (2017.01) |

(52) U.S. Cl.
CPC .............. *A61K 31/337* (2013.01); *A61K 9/08* (2013.01); *A61K 47/42* (2013.01); *A61K 47/643* (2017.08)

(58) Field of Classification Search
None
See application file for complete search history.

(56) References Cited

U.S. PATENT DOCUMENTS

| | | |
|---|---|---|
| 8,357,811 B2 | 1/2013 | Liao |
| 8,410,294 B2 | 4/2013 | Cho et al. |
| 2005/0282734 A1 | 12/2005 | Kadima et al. |
| 2007/0142457 A1 | 6/2007 | Pontiroli |
| 2010/0076008 A1 | 3/2010 | Hegedus et al. |
| 2010/0099897 A1 | 4/2010 | Kim |
| 2010/0160653 A1 | 6/2010 | Palle et al. |
| 2010/0197944 A1 | 8/2010 | Palle et al. |
| 2012/0007167 A1 | 1/2012 | Hung et al. |
| 2012/0076862 A1 | 3/2012 | Desai et al. |

FOREIGN PATENT DOCUMENTS

| | | | |
|---|---|---|---|
| CN | 103052385 A | * 4/2013 | ............ A61K 45/06 |
| WO | WO 2008/102374 | 8/2008 | |
| WO | WO 2010/091650 | 8/2010 | |
| WO | WO 2012/115402 | 8/2012 | |
| WO | WO 2014/121033 | 8/2014 | |
| WO | WO 2016/187147 | 11/2016 | |
| WO | WO 2021/158632 | 8/2021 | |

OTHER PUBLICATIONS

Cheng et al. (J. Luminescence 129 (2009) 1196-1203).*
Jiang et al. (Drug Delivery 22(2), 2015).*
Bosse et al., "Phase I Comparability of Recombinant Human Albumin and Human Serum Albumin", J Clin. Pharmacol., 45: 57-67, 2005.
Briggs et al., "An adverse reaction to the administration of disoprofol (Diprivan)", Anesthesis 37, 1099, 1982.
Bruno et al., "Population Pharmacokinetics/Pharmacodynamics of Docetaxel in Phase II Studies in Patients With Cancer", J Clin Oncol., 16: 187-96, 1998.
Carter et al., "Structure of Serum Albumin", Adv. Protein. Chem., 45, 153-203, 1994.
Chen et al., "Human serum albumin from recombinant DNA technology: Challenges and strategies", Biochimica et Biophysica Acta., 1830: 5515-5525, 2013.
Chen, "Removal of Fatty Acids from Serum Albumin by Charcoal Treatment", J Biol. Chem., 242: 173-181, 1967.
Cohn et al., "Preparation and Properties of Serum and Plasma Proteins. IV. A System for the Separation into Fractions of the Protein and Lipoprotein Components of Biological Tissues and Fluids", J Am. Chem. Soc., 68: 459-475, 1946.
Curry et al., "Crystal structure of human serum albumin complexed with fatty acid reveals an asymmetric distribution of binding sites", Nat. Struct. Biol., 5, 827-35, 1998.
Fehske et al., "The location of drug binding sites in human serum albumin", Biochem. Pharmcol., 30, 687-92, 1981.
Finlayson, "Albumin products", Seminars in Thrombosis and Hemostasis, 6, 85-120, 1980.

(Continued)

*Primary Examiner* — Shirley V Gembeh
(74) *Attorney, Agent, or Firm* — Fish & Richardson P.C.

(57) ABSTRACT

This document relates to non-covalently bound complexes including Docetaxel and human serum albumin, and to compositions comprising such complexes. This document also relates to compositions comprising Docetaxel and human serum albumin, wherein the composition is a clear aqueous solution when the composition is dissolved in an aqueous solution, and wherein the composition has a solubility in an aqueous solution of at least 10 mg/ml. This document also relates to compositions comprising Docetaxel and human serum albumin, wherein the Docetaxel and the human serum albumin in the composition have a weight ratio from about 1:50 to about 1:1000. This document also relates to compositions consisting essentially of Docetaxel and human serum albumin, wherein the Docetaxel and the human serum albumin in the composition have a weight ratio from about 1:50 to about 1:1000. The pH of the docetaxel compositions of the present disclosure is from about 5 to about 8.

13 Claims, 1 Drawing Sheet

(56) References Cited

OTHER PUBLICATIONS

Goodman et al., The Pharmacological Basis of Therapeutics, 9th ed, McGraw-Hill New York, 1996.
Hauser et al., "Oxygen transport responses to colloids and crystalloids in critically ill surgical patients.", Surgery, Gynecology and Obstetrics, 150, 811-816, 1980.
He et al., "Atomic structure and chemistry of human serum albumin", Nature, 358, 209-15, 1992.
International Preliminary Report on Patentability in Appln. No. PCT/US2017/058697, dated Apr. 30, 2019, 6 pages.
Kragh-Hansen, "Structure and ligand binding properties of human serum albumin", Dan. Med Bull., 1441, 131-40, 1990.
Lee et al., "An intravenous formulation decision tree for discovery compound formulation development", International Journal of Pharmaceutics 253, 111-119, 2003.
Lin et al., "Stability of Human Serum Albumin During Bioprocessing: Denaturation and Aggregation During Processing of Albumin Paste", Pharmaceutical Research, 17:391-6, 2000.
Piccart et al., "Docetaxel: an Active New Drug for Treatment of Advanced Epithelial Ovarian Cancer", J. Natl Cancer Inst., 87: 676-81, 1995.
Sugio et al., "Crystal structure of human serum albumin at 2.5 Å resolution", Protein. Eng., 12, 439-46, 1999.
Trudeau et al., "Docetaxel in patients with metastatic breast cancer: a phase II study of the National Cancer Institute of Canada-Clinical Trials Group", J Clin Oncol 14: 422-8, 1996.
Tullis, "Albumin", JAMA, 237, 355-360, 460-463, 1977.
Vorum, "Reversible ligand binding to human serum albumin. Theoretical and clinical aspects," Dan. Med. Bull., 46, 379-99, 1999.
Waugh et al., "Stability, compatibility, and plasticizer extraction of taxol (NSC-125973) injection diluted in infusion solutions and stored in various containers", Am. J Hosp. Pharmacists, 48, 1520-1524, 1991.
International Search Report and Written Opinion for Application No. PCT/US17/58697, dated Dec. 27, 2017, 13 pages.
Harm et al., "Removal of stabilizers from human serum albumin by adsorbents and dialysis used in blood purification," PLoS One, Jan. 2018, 1-18.
Abraxane, "Highlights of prescribing information," FDA labeling Aug. 2020, 24 pages.
Ali et al., "Butitaxel Analogues: Synthesis and Structure-Activity Relationships," J. Med. Chem., 1997, 40:236-241.
Taxotere, "Highlights of prescribing information", FDA label, Jun. 2019, 62 pages.
Taxol(paclitaxel) injection,"Patient infoitnation," Apr. 2011 ,53 pages.

* cited by examiner

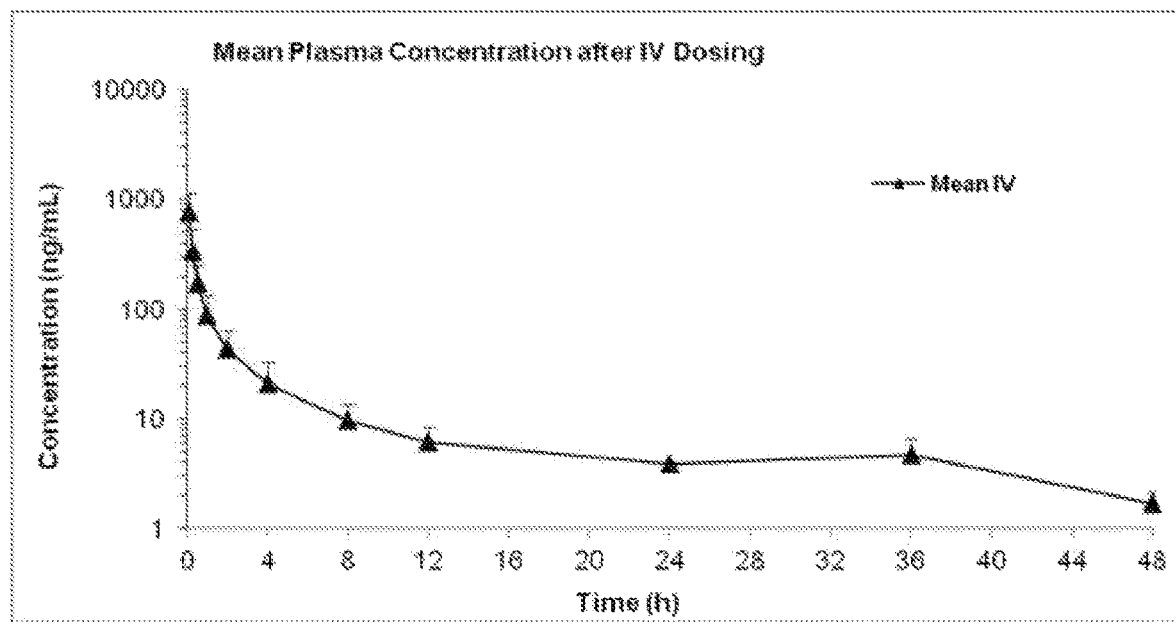

US 11,419,842 B2

NEUTRAL PH COMPOSITIONS OF DOCETAXEL AND HUMAN SERUM ALBUMIN

CLAIM OF PRIORITY

This application is a 371 U.S. National Application of PCT/US2017/058697, filed Oct. 27, 2017, which claims the benefit of U.S. Provisional Patent Applications Ser. No. 62/413,603, filed on Oct. 27, 2016, and Ser. No. 62/420,397, filed on Nov. 10, 2016. The entire contents of the foregoing are hereby incorporated by reference.

TECHNICAL FIELD

This document relates to complexes and compositions for the treatment of proliferative diseases, and more particularly to complexes and compositions comprising Docetaxel and human serum albumin, wherein pH of the compositions is neutral.

BACKGROUND

Many drugs for parenteral use are insoluble in water, and are thus formulated with solubilizing agents, surfactants, solvents, and/or emulsifiers that are irritating, allergenic, or toxic when administered to patients. See, e.g., Briggs et al., *Anesthesis* 37, 1099 (1982), and Waugh et al., *Am. J. Hosp. Pharmacists*, 48, 1520 (1991)). Further, many of these drugs, especially those administered intravenously, cause undesirable side effects such as venous irritation, phlebitis, burning and pain on injection, venous thrombosis, extravasation, and other administration related side effects. Additionally, often free drugs present in formulations induce pain or irritation upon administration.

Taxanes play an important role in the treatment of various solid tumors. As a second-generation semi-synthetic taxane derivative, Docetaxel is about twice as potent as paclitaxel in habiting microtubule depolymerization, and has the unique ability to alter certain classes of microtubules, which differs from most spindle poisons currently used in clinic. However, Docetaxel has very poor water solubility. The clinical intravenous administration of commercially available Docetaxel (Taxotere®) is formulated in a highly concentrated solution containing 40 mg Docetaxel and 1040 mg Polysorbate 80 per mL. This concentrated solution must be carefully diluted with solvent containing 13% ethanol in saline before administration, and must be used within 4 hours due to its limited stability. These attributes limit the administration of Docetaxel. Further, it has been reported that docetaxel administration is associated with the occurrence of unpredictable (acute) hypersensitivity reactions and cumulative fluid retention. See, e.g., Trudeau M E et al., *J Clin Oncol* 1996; 14:422-8, Piccart M J et al., *J Natl Cancer Inst* 1995; 87:676-81, Bruno R et al., *J Clin Oncol* 1998; 16:187-96. These side-effects have been attributed, in part, to the presence of polysorbate 80.

US 2005/0282734 describes complexes of paclitaxel and albumin. Successful formulations described in this document require acidic pH.

WO 2014/121033 describes complexes of camptothecin and albumin.

US 2012/0076862 describes nanoparticles of taxane and albumin.

US 2010/0076008 describe paclitaxel non-covalently bound to HSA.

WO 2016/187147 describes complexes of docetaxel and albumin.

Accordingly, there is a need in the art for stable and non-toxic formulations of Docetaxel. The compositions and methods described in the present application help meet this need.

SUMMARY

Provided herein are non-covalently bound complexes including Docetaxel and human serum albumin, wherein the Docetaxel and the human serum albumin are in a molar ratio from about 0.1:1 to about 5:1. In some embodiments, the pH of a composition comprising the non-covalently bound complexes including Docetaxel and human serum albumin is neutral (e.g., pH of the composition is from about 5 to about 8, from about 5.5 to about 7.5, or from about 6 to about 7, or the pH of the composition is about 5, about 5.5, about 6, about 6.4, about 6.5, about 6.6, about 7, about 7.5 or about 8).

In some embodiments, the Docetaxel and the human serum albumin have a molar ratio from about 0.1:1 to about 3:1, from about 0.5:1 to about 2:1, from about 0.75:1 to about 1.5:1, or from about 0.8:1 to about 1.3:1. In some embodiments, the Docetaxel and the human serum albumin have a molar ratio of about 0.5:1, about 0.6:1, about 0.7:1, about 0.8:1, about 0.9:1, about 1:1, about 1.1:1, about 1.2:1, about 1.3:1, about 1.4:1, or about 1.5:1.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

Also, provided herein is a non-covalently bound complex including Docetaxel and human serum albumin, wherein the Docetaxel and the human serum albumin are in a molar ratio from about 0.1:1 to about 5:1.

The present application also provides a non-covalently bound complex comprising Docetaxel and human serum albumin, wherein molar ratio of the Docetaxel and the human serum albumin in the complex is from about 0.1:1 to about 5:1.

In some embodiments, the molar ratio of Docetaxel and the human serum albumin in the complex is from about 0.1:1 to about 3:1, from about 0.5:1 to about 2:1, from about 0.75:1 to about 1.5:1, or from about 0.8:1 to about 1.3:1. In some embodiments, the Docetaxel and the human serum albumin have a molar ratio of about 0.5:1, about 0.6:1, about 0.7:1, about 0.8:1, about 0.9:1, about 1:1, about 1.1:1, about 1.2:1, about 1.3:1, about 1.4:1, or about 1.5:1.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

Also, provided herein is a composition comprising a non-covalently bound complex including Docetaxel and human serum albumin, wherein the Docetaxel and the human serum albumin in the composition have a molar ratio from about 0.1:1 to about 5:1. In some embodiments, the Docetaxel and the human serum albumin have a molar ratio from about 0.1:1 to about 3:1, from about 0.5:1 to about 3:1, from about 0.5:1 to about 2:1, from about 0.75:1 to about 1.5:1, or from about 0.8:1 to about 1.3:1. In some embodiments, the Docetaxel and the human serum albumin have a molar ratio of about 0.2:1, about 0.3:1, about 0.4:1, about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, or about 2.5:1. In some embodiments, the pH of the composition comprising a non-covalently bound complex including Docetaxel and human serum albumin is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a solid formulation. For example, the solid formulation can be produced in a uniform manner by lyophilization. A skilled artisan would recognize other methods, such as rotary evaporation, that can also produce solid formulations. In some embodiments, the pH of the solid formulation is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation is free of surfactants selected from the group selected from CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water. In some embodiments, the pH of the aqueous formulation (e.g., clear aqueous solution) is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

Also, provided herein is a pharmaceutical composition comprising the composition comprising a non-covalently bound complex including the Docetaxel and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising the composition comprising a non-covalently bound complex comprising the Docetaxel and the human serum albumin as described herein, and a pharmaceutically acceptable carrier.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

Also, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the composition has a solubility in an aqueous solution of at least 10 mg/ml. In some aspects of these embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the Docetaxel and the human serum albumin have a molar ratio from about 0.1:1 to about 3:1, from about 0.2:1 to about 3:1, from about 0.2:1 to about 2:1, from about 0.5:1 to about 2:1, from about 0.75:1 to about 1.5:1, or from about 0.8:1 to about 1.3:1. In some embodiments, the Docetaxel and the human serum albumin have a molar ratio of about 0.2:1, about 0.3:1, about 0.4:1, about 0.5:1, about 0.6:1, about 0.7:1, about 0.8:1, about 0.9:1, about 1:1, about 1.1:1, about 1.2:1, about 1.3:1, about 1.4:1, or about 1.5:1, about 1.6:1, about 1.7:1, about 1.8:1, about 1.9:1, about 2:1, about 2.1:1, about 2.2:1, about 2.3:1, about 2.4:1, or about 2.5:1.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition forms a clear aqueous solution for at least 6 hours when the composition is dissolved in an aqueous solution. In some embodiments, the composition forms a clear aqueous solution for at least 24 hours when the composition is dissolved in an aqueous solution. In some embodiments, the composition forms a clear aqueous solution for at least 3 days when the composition is dissolved in an aqueous solution. In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations. In some aspects of these embodiments, the pH of the solid formulation is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation is free of surfactants selected from the group selected from CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water. In some embodiments, the solution remains clear for at least about 2 hours, 4 hours, 6 hours, 8 hours, 10 hours, 12 hours, 20 hours, 24 hours, 2 days, 3 days, 4 days, 5 days, 6 days or a week. In some embodiments, the pH of the aqueous formulation is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

Also, provided herein is a pharmaceutical composition comprising the composition comprising the Docetaxel and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising the composition comprising the Docetaxel and the human serum albumin as described herein, and a pharmaceutically acceptable carrier.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

Also, provided herein is a composition comprising Docetaxel and human serum albumin, wherein the Docetaxel and the human serum albumin in the composition have a ratio by weight from about 1:50 to about 1:1000. In some embodiments, the pH of a composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the Docetaxel and the human serum albumin in the composition are in a ratio by weight from about 1:50 to about 1:500. In some embodiments, the Docetaxel and the human serum albumin in the composition are in a ratio by weight from about 1:60 to about 1:300. In some embodiments, the Docetaxel and the human serum albumin in the composition are in a ratio by weight from about 1:70 to about 1:250. In some embodiments, the Docetaxel and the human serum albumin in the composition are in a ratio by weight from about 1:80 to about 1:200. In some embodiments, the Docetaxel and the human serum albumin in the composition are in a ratio by weight from about 1:90 to about 1:120. In some embodiments, the Docetaxel and the human serum albumin in the composition are in a ratio by weight from about 1:70 to about 1:1000. In some embodiments, the Docetaxel and the human serum albumin in the composition are in a ratio by weight from about 1:80 to about 1:1000. In some embodiments, the Docetaxel and the human serum albumin in the composition are in a ratio by weight from about 1:90 to about 1:1000. In some embodiments, the Docetaxel and the human serum albumin in the composition are in a ratio by weight from about 1:100 to about 1:1000. In some embodiments, the Docetaxel and the human serum albumin in the composition are in a ratio by weight from about 1:70 to about 1:500. In some embodiments, the Docetaxel and the human serum albumin in the composition are in a ratio by weight from about 1:80 to about 1:500. In some embodiments, the Docetaxel and the human serum albumin in the composition are in a ratio by weight from about 1:90 to about 1:500. In some embodiments, the Docetaxel and the human serum albumin in the composition are in a ratio by weight from about 1:100 to about 1:500. In some embodiments, the Docetaxel and the human serum albumin in the composition are in a ratio by weight of about 1:60, about 1:70, about 1:80, about 1:90, about 1:100, about 1:110, about 1:120, about 1:130, about 1:140, about 1:150, about 1:160, about 1:170, about 1:180, about 1:190, about 1:200, about 1:210, about 1:220, about 1:230, about 1:240, or about 1:250.

In some embodiments, the human serum albumin is a native human serum albumin. In some embodiments, the human serum albumin is a recombinant human serum albumin. In some embodiments, the human serum albumin is essentially fatty acid free. In some embodiments, the human serum albumin is fatty acid free.

In some embodiments, the composition is a clear aqueous solution when the composition is dissolved in an aqueous solution. In some embodiments, the aqueous solution is substantially free of solvent other than water.

In some embodiments, the composition forms a clear aqueous solution for at least 3 hours when the composition is dissolved in an aqueous solution. In some embodiments, the composition forms a clear aqueous solution for at least 6 hours when the composition is dissolved in an aqueous solution. In some embodiments, the composition forms a clear aqueous solution for at least 24 hours when the composition is dissolved in an aqueous solution. In some embodiments, the composition forms a clear aqueous solution for at least 3 days when the composition is dissolved in an aqueous solution. In some embodiments, the aqueous solution is substantially free of solvent other than water. In some embodiments, the pH of the aqueous solution is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the composition is a solid formulation. In some embodiments, the composition is an aqueous formulation. In some embodiments, the aqueous formulation is substantially free of solvent other than water. In some embodiments, the aqueous formulation is free of a surfactant, such as CREMOPHOR® surfactants and Polysorbate 80. In some embodiments, the aqueous formulation is a clear aqueous solution. In some embodiments, the aqueous formulation is free of surfactants selected from the group selected from CREMOPHOR® surfactants and Polysorbate 80. In some embodiments, the pH of the solid formulation or the aqueous formulation is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

Also, provided herein is a pharmaceutical composition comprising the composition comprising the Docetaxel and the human serum albumin as described herein, and a pharmaceutically acceptable carrier.

Also, provided herein is a method of treating cancer comprising the step of administering to a subject in need thereof a therapeutically effective amount of a pharmaceutical composition comprising the composition comprising the Docetaxel and the human serum albumin as described herein, and a pharmaceutically acceptable carrier.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

Also, provided herein is a composition consisting essentially of Docetaxel and human serum albumin, wherein the Docetaxel and the human serum albumin in the composition have a ratio by weight from about 1:50 to about 1:1000.

In some embodiments, the Docetaxel and the human serum albumin in the composition are in a ratio by weight from about 1:50 to about 1:500. In some embodiments, the Docetaxel and the human serum albumin in the composition are in a ratio by weight from about 1:60 to about 1:300. In some embodiments, the Docetaxel and the human serum albumin in the composition are in a ratio by weight from about 1:70 to about 1:250. In some embodiments, the Docetaxel and the human serum albumin in the composition are in a ratio by weight from about 1:80 to about 1:200. In some embodiments, the Docetaxel and the human serum albumin in the composition are in a ratio by weight from about 1:90 to about 1:120. In some embodiments, the Docetaxel and the human serum albumin in the composition are in a ratio by weight from about 1:70 to about 1:1000. In some embodiments, the Docetaxel and the human serum albumin in the composition are in a ratio by weight from about 1:80 to about 1:1000. In some embodiments, the Docetaxel and the human serum albumin in the composition are in a ratio by weight from about 1:90 to about 1:1000. In some embodiments, the Docetaxel and the human serum albumin in the composition are in a ratio by weight from about 1:100 to about 1:1000. In some embodiments, the Docetaxel and the human serum albumin in the composition are in a ratio by weight from about 1:70 to about 1:500. In some embodiments, the Docetaxel and the human serum albumin in the composition are in a ratio by weight from about 1:80 to about 1:500. In some embodiments, the Docetaxel and the human serum albumin in the composition are in a ratio by weight from about 1:90 to about 1:500. In some embodiments, the Docetaxel and the human serum albumin in the composition are in a ratio by weight from about 1:100 to about 1:500. In some embodiments, the Docetaxel and the human serum albumin in the composition are in a ratio by weight of about 1:60, about 1:70, about 1:80, about 1:90, about 1:100, about 1:110, about 1:120, about 1:130, about 1:140, about 1:150, about 1:160, about 1:170, about 1:180, about 1:190, about 1:200, about 1:210, about 1:220, about 1:230, about 1:240, or about 1:250.

DESCRIPTION OF DRAWINGS

FIG. 1 is a graph showing mean plasma concentration over time for Docetaxel after an IV dose of 680 mg/kg of the composition comprising Docetaxel and HSA in SD rats.

DETAILED DESCRIPTION

Provided herein are non-covalently bound complexes including Docetaxel and human serum albumin, wherein the Docetaxel and the human serum albumin are in a molar ratio from about 0.1:1 to about 5:1. In some embodiments, the pH of a composition comprising the non-covalently bound complexes including Docetaxel and human serum albumin is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the present disclosure provides a non-covalently bound complex comprising Docetaxel and human serum albumin, wherein the molar ratio of Docetaxel and the human serum albumin in each complex is from about 0.1:1 to about 5:1.

In some embodiments, the present disclosure provides non-covalently bound complexes comprising Docetaxel and human serum albumin, wherein the molar ratio of Docetaxel and the human serum albumin in the complexes is from about 0.1:1 to about 5:1.

In some embodiments, the molar ratio of Docetaxel and the human serum albumin in the complex is from about 0.1:1 to about 3:1, from about 0.5:1 to about 2:1, from about 0.75:1 to about 1.5:1, or from about 0.8:1 to about 1.3:1. In some embodiments, the Docetaxel and the human serum albumin have a molar ratio of about 0.5:1, about 0.6:1, about 0.7:1, about 0.8:1, about 0.9:1, about 1:1, about 1.1:1, about 1.2:1, about 1.3:1, about 1.4:1, or about 1.5:1.

In some embodiments, the non-covalent interaction between Docetaxel and human serum albumin in the complex comprises hydrogen bonding. In some embodiments, the non-covalent interaction between Docetaxel and human serum albumin in the complex comprises electrostatic interaction. In some embodiments, the non-covalent interaction between Docetaxel and human serum albumin in the complex comprises hydrophobic interaction. In some embodiments, the non-covalent interaction between Docetaxel and human serum albumin in the complex comprises Van der Waals forces.

As used herein, the term "human serum albumin" refers to native and recombinant human serum albumin. Native human serum albumin and other plasma proteins can be precipitated from human plasma by varying the pH and adding ethanol, in what is known as the Cohn fractionation process (Cohn E J et al., *J. Am. Chem. Soc.* 1946; 68:459-475). By controlling the pH and ethanol content, semi-purified fractions of plasma proteins can be produced. One of the last proteins to precipitate in the Cohn process is native human serum albumin. After precipitation, a wet paste of crude native human serum albumin is obtained. Subsequent bioprocessing steps (purification, filtration, pasteurization, etc.) can be used to produce a purified, stabilized form of native human serum albumin for commercial use (Lin J J et al., *Pharmaceutical Research* 2000; 17:391-6). Recombinant human serum albumin is a highly purified animal-, virus-, and prion-free product as alternative to native human serum albumin, to which it is structurally equivalent (Bosse D et al., *J. Clin. Pharmacol.* 2005; 45:57-67). Recombinant human serum albumin has been produced by various hosts, both prokaryotic and eukaryotic (Chen Z et al., *Biochimica et Biophysica Acta* 2013; 1830:5515-5525). A fatty acid free human serum albumin can be prepared by treatment of human serum albumin with charcoal at low pH. Likewise, treatment of human serum albumin with charcoal at low pH can be used to remove fatty acids from human serum albumin (Chen R F, *J. Biol. Chem.* 1967; 242:173-181). Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)).

Human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., *The Pharmacological Basis of Therapeutics*, 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (1981), Vorum, Dan. Med. Bull., 46, 379-99 (1999), Kragh-Hansen, Dan. *Med Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (1992), and Carter et al., *Adv. Protein. Chem.*, 45, 153-203 (1994)).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

As used herein, the term "non-covalently bound complex" refers to a complex in which the bonds between the components of the complex are non-covalent bonds (e.g., weak bonds such as hydrogen bonds, electrostatic effects, π-effects, hydrophobic effects and Van der Waals forces). Further, human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., The Pharmacological Basis of Therapeutics, 9th ed, McGraw-Hill New York (1996)). Additionally, after the drug molecule binds to HSA, the drug molecule and HSA form a non-covalently bound drug and protein complex through the binding sites of HSA. This concept is commonly understood by one of ordinary skill in the art to which this disclosure belongs. One example of a non-covalently bound complex is a non-covalently bound complex of HSA and fatty acids, in which the fatty acids bind to HSA through HSA's multiple binding sites.

As used herein, the term "stable" refers to non-covalently bound complexes that do not readily disassociate and aggregate into their separate parts, e.g., do not readily dissociate and aggregate for a period of time of greater than 6 hours, 12 hours, 24 hours, or 3 days). For example, a solution including stable non-covalently bound complexes will often appear transparent whereas a solution including unstable non-covalently bound complexes will appear translucent or cloudy. Further, it will be appreciated by those of ordinary skill in the art, that after a period of time, stable non-covalently bound complexes can disassociate and aggregate into their separate parts. Thus, a solution including stable non-covalently bound complexes can become translucent or cloudy after a period of time (e.g., 6 hours, 12 hours, 24 hours, or 3 days).

In vitro studies showed that Docetaxel is about 94% protein bound, mainly to al-acid glycoprotein, albumin, and lipoproteins. In three cancer patients, the in vitro binding to plasma proteins was found to be approximately 97%. See Docetaxel Prescribing Information.

As used herein, the term "essentially fatty acid free" refers to proteins (e.g. serum albumin) that contain less than about 0.02% fatty acid by weight. For example, human serum albumin that is essentially fatty acid free can contain less than 0.02% fatty acid by weight.

As used herein, the term "fatty acids" refers to non-esterified fatty acids (e.g. linoleic acid, α-linoleic acid, γ-linoleic acid).

As used herein the term Docetaxel is a compound that has the CAS No. 114977-28-5 and the following chemical structure:

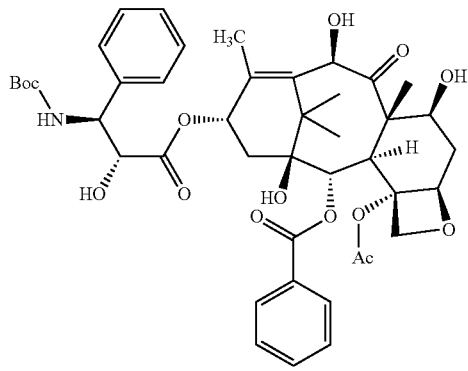

Docetaxel is a white to almost-white powder. It is highly lipophilic and practically insoluble in water.

Further, Docetaxel is a microtubule inhibitor indicated for breast cancer, non-small cell lung cancer, hormone refractory prostate cancer, gastric adenocarcinoma, and squamous cell carcinoma of the head and neck cancer.

In some embodiments, the Docetaxel can be a pharmaceutically acceptable salt of Docetaxel.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. In some embodiments, pharmaceutically acceptable salts may be preferred over the respective free base or free acid because such salts impart greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, hydrogen bisulfide, bitartrate, gluconate, glucuronate, para-bromophenylsulfonate, carbonate, pyrosulfate, sulfite, bisulfite, monohydrogen phosphate, dihydrogen phosphate, metaphosphate, pyrophosphate, chloride, bromide, iodide, decanoate, caprylate, caprate, propiolate, suberate, sebacate, butyne-1,4-dioate, hexyne-1,6-dioate, terephthalate, sulfonate, xylenesulfonate, phenylpropionate, phenylbutyrate, β-hydroxybutyrate, glycolate, propanesulfonate, naphthalene-1-sulfonate, naphthalene-2-sulfonate and 2,5-dihydroxybenzoate. Suitable bases include pharmaceutically acceptable inorganic bases and pharmaceutically acceptable organic bases. Representative pharmaceutically acceptable base addition salts include hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the Docetaxel can be a Docetaxel with 1, 2, or 3 equivalents of the water solvate. In some embodiments, the Docetaxel can be a Docetaxel with three equivalents of the water solvate. In some embodiments, Docetaxel is the docetaxel trihydrate. In some embodiments, Docetaxel is the docetaxel monohydrate. In some embodiments, Docetaxel is the docetaxel anhydrous. In some embodiments, the docetaxel can be a docetaxel with one equivalent of the acetone solvate. In some embodiments, the docetaxel can be any one of docetaxel solvates disclosed, for example, in WO2010091650 or US2012007167, the disclosures of which are incorporated herein by reference in its entirety.

In some embodiments, docetaxel is crystalline. In some embodiments, docetaxel is any one of the crystalline forms disclosed, for example, in WO2012115402, U.S. Pat. No. 8,410,294, US20100197944, US20100099897, U.S. Pat.

No. 8,357,811, US20100160653, or US20070142457, the disclosures of which are incorporated herein by reference in their entirety.

In some embodiments, docetaxel in amorphous. In some embodiments. Docetaxel is any one of the amorphous forms disclosed, for example, in WO2008102374, the disclosure of which is incorporated herein by reference in its entirety.

Also, provided herein is a non-covalently bound complex including Docetaxel and human serum albumin, wherein the Docetaxel and the human serum albumin are in a molar ratio from about 0.1:1 to about 5:1.

In some embodiments, the present disclosure provides a non-covalently bound complex comprising Docetaxel and human serum albumin, wherein the molar ratio of Docetaxel and the human serum albumin in the complex is from about 0.1:1 to about 5:1.

In some embodiments, the Docetaxel and the human serum albumin have a molar ratio from about 0.1:1 to about 3:1, from about 0.5:1 to about 2:1, from about 0.75:1 to about 1.5:1, or from about 0.8:1 to about 1.3:1. In some embodiments, the Docetaxel and the human serum albumin have a molar ratio of about 0.5:1, about 0.6:1, about 0.7:1, about 0.8:1, about 0.9:1, about 1:1, about 1.1:1, about 1.2:1, about 1.3:1, about 1.4:1, or about 1.5:1.

In some embodiments, the molar ratio of Docetaxel and the human serum albumin in the complex is from about 0.1:1 to about 3:1, from about 0.5:1 to about 2:1, from about 0.75:1 to about 1.5:1, or from about 0.8:1 to about 1.3:1 In some embodiments, the molar ratio of Docetaxel and the human serum albumin in the complex is about 0.5:1, about 0.6:1, about 0.7:1, about 0.8:1, about 0.9:1, about 1:1, about 1.1:1, about 1.2:1, about 1.3:1, about 1.4:1, or about 1.5:1.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

Also, provided herein is a composition comprising a non-covalently bound complex comprising Docetaxel and human serum albumin, wherein the Docetaxel and the human serum albumin in the composition have a molar ratio from about 0.1:1 to about 5:1. In some embodiments, the present disclosure provides a composition comprising a non-covalently bound complex comprising Docetaxel and human serum albumin, wherein the molar ratio of Docetaxel and the human serum albumin in the complex is from about 0.1:1 to about 5:1. In some embodiments, the pH of a composition comprising a non-covalently bound complex including Docetaxel and human serum albumin is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the molar ratio of Docetaxel and the human serum albumin is from about 0.1:1 to about 3:1, from about 0.5:1 to about 3:1, from about 0.5:1 to about 2:1, from about 0.75:1 to about 1.5:1, or from about 0.8:1 to about 1.3:1. In some embodiments, the molar ratio of Docetaxel and the human serum albumin is about 0.2:1, about 0.3:1, about 0.4:1, about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, or about 2.5:1.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, provided herein is a composition comprising a non-covalently bound complex comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 5 to about 8.

In some embodiments, provided herein is a composition comprising a non-covalently bound complex comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 6 to about 7.5.

In some embodiments, provided herein is a composition comprising a non-covalently bound complex comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 5 to about 8.

In some embodiments, provided herein is a composition comprising a non-covalently bound complex comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 6 to about 7.5.

In some embodiments, provided herein is a composition comprising a non-covalently bound complex comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 5 to about 8.

In some embodiments, provided herein is a composition comprising a non-covalently bound complex comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 6 to about 7.5.

In some embodiments, provided herein is a composition comprising a non-covalently bound complex comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising a non-covalently bound complex comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising a non-covalently bound complex comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising a non-covalently bound complex comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising a non-covalently bound complex comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising a non-covalently bound complex comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising a non-covalently bound complex comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising a non-covalently bound complex comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising a non-covalently bound complex comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising a non-covalently bound complex comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising a non-covalently bound complex comprising Docetaxel and human serum albumin wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising a non-covalently bound complex comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the composition is a clear aqueous solution for at least 3 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 24 hours when the composition is dissolved in an aqueous solution. In some embodiments, the composition is a clear aqueous solution for at least 3 days when the composition is dissolved in an aqueous solution. In some embodiments, the aqueous solution is substantially free of solvent other than water. In some embodiments, the aqueous solution free of solvent other than water.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

In some embodiments, the composition is a solid formulation. For example, the solid formulation can be produced in a uniform manner by lyophilization. A skilled artisan would recognize other methods, such as rotary evaporation, that can also produce solid formulations. In some embodiments, the pH of the solid formulation is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents. In some embodiments, the pH of the aqueous formulation (e.g., clear aqueous solution) is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent.

In some embodiments, the aqueous formulation can be free of a surfactant. In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of surfactants and/or less than 0.0005%, less than 0.0003%, or less than 0.0001% of surfactant.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

As used herein, the term "clear aqueous solution" refers to a solution containing Docetaxel and HSA in a water containing solution that is transparent upon visual observation and essentially free of visible particles or precipitation of undissolved Docetaxel.

The term "essentially free of visible particles or precipitation of undissolved Docetaxel" can be assessed as follows: after a clear aqueous solution is filtered with a 0.22 micron filter, the amount of Docetaxel in the filtered aqueous solution is at least 95% of the total amount of Docetaxel in the aqueous solution before filtration. The total amount of Docetaxel in the aqueous solution before filtration includes the particles or precipitation of undissolved Docetaxel in the aqueous solution or with the aqueous solution. The amount of the Docetaxel in an aqueous solution can be measured by the methods using HPLC. The methods of measuring the amount of the Docetaxel in an aqueous solution are illustrated in the experimental examples described herein. The methods are commonly understood by one of ordinary skill in the art to which this disclosure belongs.

When visually observed, for example, the term "clear aqueous solution" excludes a milky aqueous solution. Further, the term "clear aqueous solution" excludes a cloudy or hazy aqueous solution.

As used herein, the term "micron" refers to a unit of measure of one one-thousandth of a millimeter. In some embodiments, the term "micron" refers to a micrometer.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline solution. In some embodiments, the aqueous formulation is a clear aqueous solution reconstituted from the solid formulation (e.g. the sterile lyophilized powder) in 5% Dextrose water solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the aqueous formulation has pH value from about 5 to about 8. In some embodiments, the aqueous formulation is a clear aqueous solution reconstituted from the solid formulation (e.g. the sterile lyophilized powder) in 5% Dextrose water solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 ml of the aqueous solvent. In some aspects of the aforementioned embodiments, the concentration of the reconstituted solid in the aqueous formulation is from about 10 mg per 1 ml to about 500 mg per 1 ml of the aqueous solvent. In some aspects of the aforementioned embodiments, the concentration of the reconstituted solid in the aqueous formulation is from about 25 mg per 1 ml to about 250 mg per 1 ml of the aqueous solvent. In some aspects of the aforementioned embodiments, the concentration of the reconstituted solid in the aqueous formulation is from about 30 mg per 1 ml to about 200 mg per 1 ml of the aqueous solvent. In some aspects of the aforementioned embodiments, the concentration of the reconstituted solid in the aqueous formulation is from about 40 mg per 1 ml to about 150 mg per 1 ml of the aqueous solvent. In some aspects of the aforementioned embodiments, the concentration of the reconstituted solid in the aqueous formulation is from about 50 mg per 1 ml to about 125 mg per 1 ml of the aqueous solvent.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6.7 to about 7.1. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 6.7 to about 7.1. In some aspects of the aforementioned embodiments, the concentration of the reconstituted solid in the aqueous formulation is about 25 mg, about 50 mg, about 75 mg, about 100 mg, about 150 mg or 200 mg per 1 ml of the aqueous solvent. In some aspects of the aforementioned embodiments, the concentration of the reconstituted solid in the aqueous formulation is from about 10 mg per 1 ml to about 500 mg per 1 ml of the aqueous solvent. In some aspects of the aforementioned embodiments, the concentration of the reconstituted solid in the aqueous formulation is from about 25 mg per 1 ml to about 250 mg per 1 ml of the aqueous solvent. In some aspects of the aforementioned embodiments, the concentration of the reconstituted solid in the aqueous formulation is from about 30 mg per 1 ml to about 200 mg per 1 ml of the aqueous solvent. In some aspects of the aforementioned embodiments, the concentration of the reconstituted solid in the aqueous formulation is from about 40 mg per 1 ml to about 150 mg per 1 ml of the aqueous solvent. In some aspects of the aforementioned embodiments, the concentration of the reconstituted solid in the aqueous formulation is from about 50 mg per 1 ml to about 125 mg per 1 ml of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the aqueous formulation has pH value from about 6 to about 7.5. In some embodiments, the aqueous formulation is a clear aqueous solution reconstituted from the solid formulation (e.g. the sterile lyophilized powder) in 5% Dextrose water solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after a clear aqueous solution is filtered by a 0.22 micron filter, the amount of Docetaxel in the filtered aqueous solution is at least 96% of the total amount of Docetaxel in the aqueous solution before filtration. In some embodiments, after a clear aqueous solution is filtered by a 0.22 micron filter, the amount of Docetaxel in the filtered aqueous solution is at least 97% of the total amount of Docetaxel in the aqueous solution before filtration. In some embodiments, after a clear aqueous solution is filtered by a 0.22 micron filter, the amount of Docetaxel in the filtered aqueous solution is at least 98% of the total amount of Docetaxel in the aqueous solution before filtration. In some embodiments, after a clear aqueous solution is filtered by a 0.22 micron filter, the amount of Docetaxel in the filtered aqueous solution is at least 99% of the total amount of Docetaxel in the aqueous solution before filtration. In some embodiments, after a clear aqueous solution is filtered by a 0.22 micron filter, the amount of Docetaxel in the filtered aqueous solution is at least 99.5% of the total amount of Docetaxel in the aqueous solution before filtration. In some embodiments, the aqueous formulation is substantially free of solvent other than water.

In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 6 to about 7.5, and wherein the clear aqueous solution is free of solvent other than water.

In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

In some embodiments, the aqueous formulation is an aqueous solution, wherein after the aqueous solution is filtered by a 0.22 micron filter, the amount of Docetaxel in the filtered aqueous solution is at least 80% of the total amount of Docetaxel in the aqueous solution before filtration. In some embodiments, the aqueous formulation is an aqueous solution, wherein after the aqueous solution is filtered by a 0.22 micron filter, the amount of Docetaxel in the filtered aqueous solution is at least 85% of the total amount of Docetaxel in the aqueous solution before filtration. In some embodiments, the aqueous formulation is an aqueous solution, wherein after the aqueous solution is filtered by a 0.22 micron filter, the amount of Docetaxel in the filtered aqueous solution is at least 90% of the total amount of Docetaxel in the aqueous solution before filtration.

Also, provided herein is a pharmaceutical composition comprising the composition comprising a non-covalently bound complex comprising the Docetaxel and the human serum albumin as described herein, and a pharmaceutically acceptable carrier.

In some embodiments, the pharmaceutical composition further comprises at least one anti-cancer drug (e.g., any one of the anti-cancer drugs as described herein).

As used herein, the term "pharmaceutically acceptable carrier" is meant any solution used to solubilize and deliver an agent to a subject. A desirable pharmaceutically acceptable carrier is saline. Other pharmaceutically acceptable carrier and their formulation are known to one skilled in the art and described, for example, in Remington's Pharmaceutical Sciences. (20$^{th}$ edition), ed. A. Gennaro, 2003, Lippincon Williams & Wilkins.

Pharmaceutically acceptable carriers that may be used in the pharmaceutical compositions of the present application include, but are not limited to, ion exchangers, alumina, aluminum stearate, lecithin, serum proteins (other than HSA), buffer substances such as phosphates, glycine, sorbic acid, potassium sorbate, salts or electrolytes, such as protamine sulfate, disodium hydrogen phosphate, potassium hydrogen phosphate, sodium chloride, zinc salts, colloidal silica, magnesium trisilicate, and cellulose-based substances.

In some embodiments, the pharmaceutical composition is free of a surfactant, such as CREMOPHOR® surfactants and Polysorbate 80.

In some embodiments, the pharmaceutical composition is substantially free of a surfactant, such as CREMOPHOR® surfactants and Polysorbate 80. In some embodiments, the pharmaceutical composition is free of a surfactant selected from the group consisting of CREMOPHOR® surfactants and Polysorbate 80.

Also, provided herein is a method of treating a proliferative disease comprising the step of administering to a subject in need thereof a therapeutically effective amount of a pharmaceutical composition as described herein.

As used herein, the terms "individual", "patient", or "subject" are used interchangeably and refer to any animal, including mammals, preferably mice, rats, other rodents, rabbits, dogs, cats, swine, cattle, sheep, horses, or primates, and most preferably humans.

As used herein, the term "proliferative disease" refers to a disease caused by excessive proliferation of cells and turnover of cellular matrix. Non-limiting examples of proliferative diseases include cancer, atherosclerosis, arthritis (e.g. rheumatoid arthritis), psoriasis, fibrosis (e.g. pulmonary fibrosis, idiopathic pulmonary fibrosis), scleroderma and cirrhosis (e.g. cirrhosis of the liver).

Also, provided herein is a method of treating a cancer, the method comprising the step of administering to a subject in need thereof of a therapeutically effective amount of a pharmaceutical composition comprising the composition comprising a non-covalently bound complex comprising the Docetaxel and the human serum albumin as described herein, and a pharmaceutically acceptable carrier.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancer is selected from sarcoma, angiosarcoma, fibrosarcoma, rhabdomyosarcoma, liposarcoma, myxoma, rhabdomyoma, fibroma, lipoma, teratoma, non-small cell lung cancer (NSCLC), bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

As used herein, an "effective amount," "therapeutically effective amount," or a "pharmaceutically-effective amount" in reference to the compounds or compositions of the instant invention refers to the amount sufficient to induce a desired biological, pharmacological, or therapeutic outcome in a subject. That result can be reduction, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, mitigation, limitation, and/or, delay of the deleterious physiological manifestations, growth or metastases of neoplasms.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

In some embodiments, the method of treating cancer (e.g. any one of cancers described herein) comprises the step of administering to a subject in need thereof of a therapeutically effective amount of a composition comprising a non-covalently bound complex comprising the Docetaxel and the human serum albumin as described herein, and a therapeutically effective amount of at least one inhibitor of the following kinases for the treatment of cancer: PIM, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFaR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the method of treating cancer (e.g. any one of cancers described herein) comprises the step of administering to a subject in need thereof of a therapeutically effective amount of a pharmaceutical composition comprising the composition comprising a non-covalently bound complex comprising the Docetaxel and the human serum albumin as described herein, and a therapeutically effective amount of at least one anti-cancer drug. Examples of an anti-cancer drug include aberaterone, aberaterone acetate, abarelix, aldesleukin, alemtuzumab, alitretinoin, allopurinol, altretamine, anastrozole, arsenic trioxide, asparaginase, azacitidine, bavituximab, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, enzalutamide, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, a composition comprising a non-covalently bound complex comprising the Docetaxel and the human serum albumin as described herein and an anti-cancer drug are administered simultaneously.

In some embodiments, a composition comprising a non-covalently bound complex comprising the Docetaxel and the human serum albumin as described herein and an anti-cancer drug are administered consecutively.

The composition comprising a non-covalently bound complex comprising the Docetaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of Docetaxel will be approximately those already employed in clinical therapies wherein Docetaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for Docetaxel.

Also, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the composition has a solubility in an aqueous solution of at least 10 mg/ml. In some aspects of these embodiments, pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the present disclosure provides a composition comprising Docetaxel and human serum albumin, wherein the molar ratio of Docetaxel and the human serum albumin in the composition is from about 0.1:1 to about 5:1, wherein the composition forms a clear aqueous solution when the composition is dissolved in an aqueous solution, and wherein the solubility of the composition in the aqueous solution is at least 10 mg/ml. In some aspects of these embodiments, pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the composition has a solubility in an aqueous solution of about 10 mg/ml, about 20 mg/ml, about 30 mg/ml, about 40 mg/ml, about 50 mg/ml, 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, or about 200 mg/ml.

In some embodiments, the solubility of the composition in an aqueous solution is at least about 10 mg/ml, at least about 20 mg/ml, at least about 30 mg/ml, at least about at least 40 mg/ml, at least about 50 mg/ml, at least 60 mg/ml, at least about 70 mg/ml, at least about 80 mg/ml, at least about 90 mg/ml, at least about 100 mg/ml, at least about 150 mg/ml, or at least about 200 mg/ml.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C. Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6 to about 7, from about 3 to about 5, from about 3 to about 7, from about 4 to about 6, or from about 6 to about 6. In some embodiments, the pH of the buffer is about 4, about 5, about 6, about 6.4, about 6.5, about 6.6, about 7, about 7.5, or about 8. In other embodiments, aqueous solution is 0.9% saline (wherein the pH of 0.9% saline is from about 4 to about 6, from about 4.5 to about 6, or from about 5 to about 6, or wherein the pH of 0.9% saline is about 5, about 5.2, about 5.4, about 5.5, or about 6). In yet other embodiments, aqueous solution is 5% dextrose solution (wherein the pH of 5% dextrose solution is from about 3 to about 5, from about 3.5 to about 5, or from about 4 to about 5, or wherein the pH of 5% dextrose solution is about 4, about 4.2, about 4.4, about 4.5, or about 5).

As used herein, the term "aqueous solvent" refers to a liquid comprising at least 50%, at least 60%, at least 70%, at least 90% or at least 95% water. In some embodiments, aqueous solvent is water.

In some embodiments, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 5 to about 8.

In some embodiments, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 6 to about 7.5.

In some embodiments, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising Docetaxel and human serum albumin, wherein the Docetaxel and the human serum albumin in the composition have a molar ratio from about 0.1:1 to about 5:1, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, the Docetaxel and the human serum albumin have a molar ratio in the composition from about 0.1:1 to about 3:1, from about 0.2:1 to about 3:1, from about 0.2:1 to about 2:1, from about 0.5:1 to about 2:1, from about 0.75:1 to about 1.5:1, or from about 0.8:1 to about 1.3:1. In some embodiments, the Docetaxel and the human serum albumin have a molar ratio in the composition of about 0.2:1, about 0.3:1, about 0.4:1, about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, or about 2.5:1.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the Docetaxel can be a pharmaceutically acceptable salt of Docetaxel. In some embodiments, the Docetaxel can be a Docetaxel with three equivalents of the water solvate. In some embodiments, Docetaxel can be any one of crystal forms, amorphous forms, solvates and hydrates as described herein.

In some embodiments, provided herein is a composition comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 5 to about 8.

In some embodiments, provided herein is a composition comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 6 to about 7.5.

In some embodiments, provided herein is a composition comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising Docetaxel and human serum albumin, wherein the Docetaxel and the human serum albumin in the composition have a molar ratio from about 1.2:1 to about 0.3:1, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 5 to about 8.

In some embodiments, provided herein is a composition comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 6 to about 7.5.

In some embodiments, provided herein is a composition comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising Docetaxel and human serum albumin, wherein the Docetaxel and the human serum albumin in the composition have a molar ratio from about 1.1:1 to about 0.5:1, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 5 to about 8, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 6 to about 7.5, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 5 to about 8, and wherein the clear aqueous solution is free of solvent other than water. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 6 to about 7.5, and wherein the clear aqueous solution is free of solvent other than water.

In some embodiments, the composition forms a clear aqueous solution for at least 6 hours when the composition is dissolved in an aqueous solution. In some embodiments, the composition forms a clear aqueous solution for at least 24 hours when the composition is dissolved in an aqueous solution. In some embodiments, the composition forms a clear aqueous solution for at least 3 days when the composition is dissolved in an aqueous solution. In some embodiments, the aqueous solution is substantially free of solvent other than water. In some embodiments, the aqueous solution is free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% Dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% Dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 ml of the aqueous solvent. In some aspects of the aforementioned embodiments, the concentration of the reconstituted solid in the aqueous formulation is from about 10 mg per 1 ml to about 500 mg per 1 ml of the aqueous solvent. In some aspects of the aforementioned embodiments, the concentration of the reconstituted solid in the aqueous formulation is from about 25 mg per 1 ml to about 250 mg per 1 ml of the aqueous solvent. In some aspects of the aforementioned embodiments, the concentration of the reconstituted solid in the aqueous formulation is from about 30 mg per 1 ml to about 200 mg per 1 ml of the aqueous solvent. In some aspects of the aforementioned embodiments, the concentration of the reconstituted solid in the aqueous formulation is from about 40 mg per 1 ml to about 150 mg per 1 ml of the aqueous solvent. In some aspects of the aforementioned embodiments, the concentration of the reconstituted solid in the aqueous formulation is from about 50 mg per 1 ml to about 125 mg per 1 ml of the aqueous solvent.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6.7 to about 7.1. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 6.7 to about 7.1. In some aspects of the aforementioned embodiments, the concentration of the reconstituted solid in the aqueous formulation is about 25 mg, about 50 mg, about 75 mg, about 100 mg, about 150 mg or 200 mg per 1 ml of the aqueous solvent. In some aspects of the aforementioned embodiments, the concentration of the reconstituted solid in the aqueous formulation is from about 10 mg per 1 ml to about 500 mg per 1 ml of the aqueous solvent. In some aspects of the aforementioned embodiments, the concentration of the reconstituted solid in the aqueous formulation is from about 25 mg per 1 ml to about 250 mg per 1 ml of the aqueous solvent. In some aspects of the aforementioned embodiments, the concentration of the reconstituted solid in the aqueous formulation is from about 30 mg per 1 ml to about 200 mg per 1 ml of the aqueous solvent. In some aspects of the aforementioned embodiments, the concentration of the reconstituted solid in the aqueous formulation is from about 40 mg per 1 ml to about 150 mg per 1 ml of the aqueous solvent. In some aspects of the aforementioned embodiments, the concentration of the reconstituted solid in the aqueous formulation is from about 50 mg per 1 ml to about 125 mg per 1 ml of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% Dextrose solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after the aqueous formulation (e.g. a clear aqueous solution) is filtered by a 0.22 micron filter, the amount of Docetaxel in the filtered aqueous solution is at least 96% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 97% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 98% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 99% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 99.5% of the total amount of Docetaxel in the aqueous solution before filtration. In some embodiments, the aqueous formulation is substantially free of solvent other than water. In some embodiments, the aqueous formulation is free of solvent other than water.

In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 6 to about 7.5, and wherein the clear aqueous solution is free of solvent other than water.

In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours at a temperature from about 1°

C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

Also, provided herein is a pharmaceutical composition comprising the composition comprising the Docetaxel and the human serum albumin as described herein, and a pharmaceutically acceptable carrier.

In some embodiments, the pharmaceutical composition is free of a surfactant, such as CREMOPHOR® surfactants and Polysorbate 80.

In some embodiments, the pharmaceutical composition is substantially free of a surfactant, such as CREMOPHOR® surfactants and Polysorbate 80.

Also, provided herein is a method of treating a proliferative disease comprising the step of administering to a subject in need thereof a therapeutically effective amount of a pharmaceutical composition comprising the composition comprising the Docetaxel and the human serum albumin as described herein, and a pharmaceutically acceptable carrier.

Also, provided herein is a method of treating a cancer, the method comprising the step of administering to a subject in need thereof of a therapeutically effective amount of a pharmaceutical composition comprising the composition comprising the Docetaxel and the human serum albumin as described herein, and a pharmaceutically acceptable carrier.

In some embodiments, the cancer is any one of cancers described herein.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

In some embodiments, the method of treating cancer (e.g. any one of cancers described herein) comprises the step of administering to a subject in need thereof a therapeutically effective amount of a pharmaceutical composition comprising the composition comprising the Docetaxel and the human serum albumin as described herein and a therapeutically effective amount of at least one inhibitor of the kinases for the treatment of cancer described herein.

In some embodiments, the method of treating cancer (e.g. any one of cancers described herein) comprises the step of administering to a subject in need thereof a therapeutically effective amount of a pharmaceutical composition comprising the composition comprising the Docetaxel and the human serum albumin as described herein and a therapeutically effective amount of at least one anti-cancer drug described herein.

In some embodiments, a composition comprising the Docetaxel and the human serum albumin as described herein and an anti-cancer drug are administered simultaneously.

In some embodiments, a composition comprising the Docetaxel and the human serum albumin as described herein and an anti-cancer drug are administered consecutively.

The composition comprising the Docetaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of Docetaxel will be approximately those already employed in clinical therapies wherein Docetaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for Docetaxel.

Also, provided herein is a composition comprising Docetaxel and human serum albumin, wherein the Docetaxel and the human serum albumin in the composition have a ratio by weight from about 1:50 to about 1:1000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the Docetaxel and the human serum albumin in the composition are in a ratio by weight from about 1:50 to about 1:500. In some embodiments, the Docetaxel and the human serum albumin in the composition are in a ratio by weight from about 1:60 to about 1:300. In some embodiments, the Docetaxel and the human serum albumin in the composition are in a ratio by weight from about 1:70 to about 1:250. In some embodiments, the Docetaxel and the human serum albumin in the composition are in a ratio by weight from about 1:80 to about 1:200. In some embodiments, the Docetaxel and the human serum albumin in the composition are in a ratio by weight from about 1:80 to about 1:150. In some embodiments, the Docetaxel and the human serum albumin in the composition are in a ratio by weight from about 1:90 to about 1:120. In some embodiments, the Docetaxel and the human serum albumin in the composition are in a ratio by weight from about 1:70 to about 1:1000. In some embodiments, the Docetaxel and the human serum albumin in the composition are in a ratio by weight from about 1:80 to about 1:1000. In some embodiments, the Docetaxel and the human serum albumin in the composition are in a ratio by weight from about 1:90 to about 1:1000. In some embodiments, the Docetaxel and the human serum albumin in the composition are in a ratio by weight from about 1:100 to about 1:1000. In some embodiments, the Docetaxel and the human serum albumin in the composition are in a ratio by weight from about 1:70 to about 1:500. In some embodiments, the Docetaxel and the human serum albumin in the composition are in a ratio by weight from about 1:80 to about 1:500. In some embodiments, the Docetaxel and the human serum albumin in the composition are in a ratio by weight from about 1:90 to about 1:500. In some embodiments, the Docetaxel and the human serum albumin in the composition are in a ratio by weight from about 1:100 to about 1:500. In some embodiments, the Docetaxel and the human serum albumin in the composition are in a ratio by weight of about 1:60, about 1:70, about 1:80, about 1:90, about 1:100, about 1:110, about 1:120, about 1:130, about 1:140, about 1:150, about 1:160, about 1:170, about 1:180, about 1:190, about 1:200, about 1:210, about 1:220, about 1:230, about 1:240, or about 1:250.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the Docetaxel can be a pharmaceutically acceptable salt of Docetaxel. In some embodiments, the Docetaxel can be a Docetaxel with three equivalents of the water solvate. In some embodiments, Docetaxel can be any one of crystal forms, amorphous forms, solvates and hydrates as described herein.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, provided herein is a composition comprising Docetaxel and human serum albumin, wherein the Docetaxel and the human serum albumin in the composition have a ratio by weight from about 1:50 to about 1:1000, wherein the composition is a clear aqueous solution when the composition is dissolved in an aqueous solution, and wherein the clear aqueous solution has pH value from about 5 to about 8.

In some embodiments, provided herein is a composition comprising Docetaxel and human serum albumin, wherein the Docetaxel and the human serum albumin in the composition have a ratio by weight from about 1:50 to about 1:1000, wherein the composition is a clear aqueous solution when the composition is dissolved in an aqueous solution, and wherein the clear aqueous solution has pH value from about 6 to about 7.5.

In some embodiments, provided herein is a composition comprising Docetaxel and human serum albumin, wherein the Docetaxel and the human serum albumin in the composition have a ratio by weight from about 1:70 to about 1:250, wherein the composition is a clear aqueous solution when the composition is dissolved in an aqueous solution, and wherein the clear aqueous solution has pH value from about 5 to about 8.

In some embodiments, provided herein is a composition comprising Docetaxel and human serum albumin, wherein the Docetaxel and the human serum albumin in the composition have a ratio by weight from about 1:70 to about 1:250, wherein the composition is a clear aqueous solution when the composition is dissolved in an aqueous solution, and wherein the clear aqueous solution has pH value from about 6 to about 7.5.

In some embodiments, provided herein is a composition comprising Docetaxel and human serum albumin, wherein the Docetaxel and the human serum albumin in the composition have a ratio by weight from about 1:80 to about 150, wherein the composition is a clear aqueous solution when the composition is dissolved in an aqueous solution, and wherein the clear aqueous solution has pH value from about 5 to about 8.

In some embodiments, provided herein is a composition comprising Docetaxel and human serum albumin, wherein the Docetaxel and the human serum albumin in the composition have a ratio by weight from about 1:80 to about 1:150, wherein the composition is a clear aqueous solution when the composition is dissolved in an aqueous solution, and wherein the clear aqueous solution has pH value from about 6 to about 7.5.

In some embodiments, provided herein is a composition comprising Docetaxel and human serum albumin, wherein the Docetaxel and the human serum albumin in the composition have a ratio by weight from about 1:50 to about 1:1000, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising Docetaxel and human serum albumin, wherein the Docetaxel and the human serum albumin in the composition have a ratio by weight from about 1:50 to about 1:1000, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising Docetaxel and human serum albumin, wherein the Docetaxel and the human serum albumin in the composition have a ratio by weight from about 1:70 to about 1:250, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising Docetaxel and human serum albumin, wherein the Docetaxel and the human serum albumin in the composition have a ratio by weight from about 1:70 to about 1:250, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising Docetaxel and human serum albumin, wherein the Docetaxel and the human serum albumin in the composition have a ratio by weight from about 1:80 to about 1:150, wherein the composition is a clear aqueous solution when the composition is dissolved in an aqueous solution, and wherein the clear aqueous solution has pH value from about 5 to about 8, and wherein the clear aqueous solution is substantially free of solvent other than water. In some embodiments, provided herein is a composition comprising Docetaxel and human serum albumin, wherein the Docetaxel and the human serum albumin in the composition have a ratio by weight from about 1:80 to about 1:150, wherein the composition is a clear aqueous solution when the composition is dissolved in an aqueous solution, and wherein the clear aqueous solution has pH value from about 5 to about 8, and wherein the clear aqueous solution is free of solvent other than water.

In some embodiments, provided herein is a composition comprising Docetaxel and human serum albumin, wherein the Docetaxel and the human serum albumin in the composition have a ratio by weight from about 1:50 to about 1:1000, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising Docetaxel and human serum albumin, wherein the Docetaxel and the human serum albumin in the composition have a ratio by weight from about 1:50 to about 1:1000, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising Docetaxel and human serum albumin, wherein the Docetaxel and the human serum albumin in the composition have a ratio by weight from about 1:70 to about 1:250, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising Docetaxel and human serum albumin, wherein the Docetaxel and the human serum albumin in the composition have a ratio by weight from about 1:70 to about 1:250, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, provided herein is a composition comprising Docetaxel and human serum albumin, wherein the Docetaxel and the human serum albumin in the composition have a ratio by weight from about 1:80 to about 1:150, wherein the composition is a clear aqueous solution when the composition is dissolved in an aqueous solution, and wherein the clear aqueous solution has pH value from about 6 to about 7.5, and wherein the clear aqueous solution is substantially free of solvent other than water. In some embodiments, provided herein is a composition comprising Docetaxel and human serum albumin, wherein the Docetaxel and the human serum albumin in the composition have a ratio by weight from about 1:80 to about 1:150, wherein the composition is a clear aqueous solution when the composition is dissolved in an aqueous solution, and wherein the clear aqueous solution has pH value from about 6 to about 7.5, and wherein the clear aqueous solution is free of solvent other than water.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96% of the total amount of Docetaxel in the aqueous solution before the filtration. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 97% of the total amount of Docetaxel in the aqueous solution before the filtration. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 98% of the total amount of Docetaxel in the aqueous solution before the filtration. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 99% of the total amount of Docetaxel in the aqueous solution before the filtration. In some embodiments, the aqueous formulation is substantially free of solvent other than water.

In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 5 to about 8, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 6 to about 7.5, and wherein the clear aqueous solution is substantially free of solvent other than water. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 5 to about 8, and wherein the clear aqueous solution is free of solvent other than water. In some embodiments, the composition is a clear aqueous solution when the composition is dissolved in an aqueous solution, wherein after the clear aqueous solution is filtered by a 0.22 micron filter, the amount of Docetaxel in the filtered aqueous solution is at least 96%, 97%, 98%, 99%, or 99.5% of the total amount of Docetaxel in the aqueous solution before the filtration, wherein the clear aqueous solution has pH value from about 6 to about 7.5, and wherein the clear aqueous solution is free of solvent other than water.

In some embodiments, the composition is an aqueous solution, wherein after the aqueous solution is filtered by a 0.22 micron filter, the amount of Docetaxel in the filtered aqueous solution is at least 80% of the total amount of Docetaxel in the aqueous solution before the filtration. In some embodiments, the composition is an aqueous solution, wherein after the aqueous solution is filtered by a 0.22 micron filter, the amount of Docetaxel in the filtered aqueous solution is at least 85% of the total amount of Docetaxel in the aqueous solution before the filtration. In some embodiments, the composition is an aqueous solution, wherein after the aqueous solution is filtered by a 0.22 micron filter, the amount of Docetaxel in the filtered aqueous solution is at least 90% of the total amount of Docetaxel in the aqueous solution before the filtration. In some embodiments, the aqueous formulation is substantially free of solvent other than water. In some embodiments, the aqueous formulation is free of solvent other than water.

In some embodiments, the composition is a clear aqueous solution for at least 3 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 24 hours when the composition is dissolved in an aqueous solution. In some embodiments, the composition is a clear aqueous solution for at least 3 days when the composition is dissolved in an aqueous solution. In some embodiments, the aqueous solution is substantially free of solvent other than water. In some embodiments, the aqueous solution free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations. In some embodiments, the pH of the solid formulation is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the composition is an aqueous formulation. In some embodiments, the aqueous formulation is substantially free of solvent other than water. In some embodiments, the aqueous formulation is free of solvent other than water. In some embodiments, the aqueous formulation includes water and water-miscible organic solvents including at least one of polyethylene glycol 300, polyethylene glycol 400, ethanol, methanol, propylene glycol, glycerin, N-methyl-2-pyrrolidone, dimethylacetamide, and dimethylsulfoxide. For example, the water-miscible organic solvent can include ethanol. In some embodiments, the aqueous formulation includes water and ethanol. In some embodiments, the water-miscible organic solvent can be a mixture of water-miscible organic solvents. In some embodiments, the pH of the aqueous formulation (e.g., clear aqueous solution) is neutral (e.g., pH of the composition is from about 5 to about 8, from about 5.5 to about 7.5, or from about 6 to about 7, or the pH od the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5 or about 8).

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% Dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% Dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 5 to about 8. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 5 to about 8. In some aspects of the aforementioned embodiments, the concentration of the reconstituted solid in the aqueous formulation is about 25 mg, about 50 mg, about 75 mg, about 100 mg, about 150 mg or 200 mg per 1 ml of the aqueous solvent. In some aspects of the aforementioned embodiments, the concentration of the reconstituted solid in the aqueous formulation is from about 10 mg per 1 ml to about 500 mg per 1 ml of the aqueous solvent. In some aspects of the aforementioned embodiments, the concentration of the reconstituted solid in the aqueous formulation is from about 25 mg per 1 ml to about 250 mg per 1 ml of the aqueous solvent. In some aspects of the aforementioned embodiments, the concentration of the reconstituted solid in the aqueous formulation is from about 30 mg per 1 ml to about 200 mg per 1 ml of the aqueous solvent. In some aspects of the aforementioned embodiments, the concentration of the reconstituted solid in the aqueous formulation is from about 40 mg per 1 ml to about 150 mg per 1 ml of the aqueous solvent. In some aspects of the aforementioned embodiments, the concentration of the reconstituted solid in the aqueous formulation is from about 50 mg per 1 ml to about 125 mg per 1 ml of the aqueous solvent.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 5 to about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6.7 to about 7.1. In some embodiments, the aqueous formulation is a clear aqueous solution reconstituted from the solid formulation (e.g. the sterile lyophilized powder) in 5% dextrose water solution, wherein the pH of 5% dextrose solution is about 4.4, and wherein the aqueous formulation has pH value from about 6.7 to about 7.1. In some aspects of the aforementioned embodiments, the concentration of the reconstituted solid in the aqueous formulation is about 25 mg, about 50 mg, about 75 mg, about 100 mg, about 150 mg or 200 mg per 1 ml of the aqueous solvent. In some aspects of the aforementioned embodiments, the concentration of the reconstituted solid in the aqueous formulation is from about 10 mg per 1 ml to about 500 mg per 1 ml of the aqueous solvent. In some aspects of the aforementioned embodiments, the concentration of the reconstituted solid in the aqueous formulation is from about 25 mg per 1 ml to about 250 mg per 1 ml of the aqueous solvent. In some aspects of the aforementioned embodiments, the concentration of the reconstituted solid in the aqueous formulation is from about 30 mg per 1 ml to about 200 mg per 1 ml of the aqueous solvent. In some aspects of the aforementioned embodiments, the concentration of the reconstituted solid in the aqueous formulation is from about 40 mg per 1 ml to about 150 mg per 1 ml of the aqueous solvent. In some aspects of the aforementioned embodiments, the concentration of the reconstituted solid in the aqueous formulation is from about 50 mg per 1 ml to about 125 mg per 1 ml of the aqueous solvent.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% Dextrose solution, wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value from about 6 to about 7.5. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value from about 6 to about 7.5. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value from about 6 to about 7.5.

In some embodiments, the aqueous formulation is a clear aqueous solution reconstituted from the solid formulation (e.g. the sterile lyophilized powder) in water, wherein the pH of water is about 7, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 0.9% saline solution, wherein the pH of 0.9% saline solution is about 5.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8. In some embodiments, the aqueous formulation is a clear aqueous solution reconstituted from the solid formulation (e.g. the sterile lyophilized powder) in 5% dextrose water solution, wherein pH of the 5% dextrose solution is about 4.4, and wherein the aqueous formulation has pH value of about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, after the aqueous formulation (e.g. a clear aqueous solution) is filtered by a 0.22 micron filter, the amount of Docetaxel in the filtered aqueous solution is at least 96% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 97% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 98% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 99% of the total amount of Docetaxel in the aqueous solution before filtration. In some embodiments, after the aqueous formulation (e.g. a clear aqueous solution) is filtered by a 0.22 micron filter, the amount of Docetaxel in the filtered aqueous solution is at least 99.5% of the total amount of Docetaxel in the aqueous solution before filtration. In some embodiments, the aqueous formulation is substantially free of solvent other than water. In some embodiments, the aqueous formulation is free of solvent other than water.

In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of Docetaxel in the filtered aqueous solution is at least 96%, 97%, 98%, 99%, or 99.5% of the total amount of Docetaxel in the aqueous solution before filtration, wherein the clear aqueous solution has pH value from about 6 to about 7.5, and wherein the clear aqueous solution is free of solvent other than water.

In some embodiments, the aqueous formulation is a clear aqueous solution for at least 3 hours. In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a clear aqueous solution for at least 3 days when dissolved in an aqueous solution at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

Also, provided herein is a pharmaceutical composition comprising the composition comprising the Docetaxel and the human serum albumin as described herein, and a pharmaceutically acceptable carrier.

In some embodiments, the pharmaceutical composition is free of a surfactant, such as CREMOPHOR® surfactants and Polysorbate 80.

In some embodiments, the pharmaceutical composition is substantially free of a surfactant, such as CREMOPHOR® surfactants and Polysorbate 80.

Also, provided herein is a method of treating a proliferative disease comprising the step of administering to a subject in need thereof a pharmaceutical composition comprising the composition comprising the Docetaxel and the human serum albumin as described herein, and a pharmaceutically acceptable carrier.

Also, provided herein is a method of treating a cancer (e.g., any one of cancers described herein), the method comprising the step of administering to a subject in need thereof of a therapeutically effective amount of a pharmaceutical composition comprising the composition comprising the Docetaxel and the human serum albumin as described herein, and a pharmaceutically acceptable carrier.

In some embodiments, the cancer is any one of cancers described herein.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

In some embodiments, the method of treating cancer (e.g., any one of cancers described herein) comprises the step of administering to a subject in need thereof a therapeutically effective amount of a pharmaceutical composition comprising the composition comprising the Docetaxel and the human serum albumin as described herein, and a therapeutically effective amount of at least one inhibitor of the kinases for the treatment of cancer described herein.

In some embodiments, the method of treating cancer (e.g. any one of cancers described herein) comprises the step of administering to a subject in need thereof a therapeutically effective amount of a pharmaceutical composition comprising the composition comprising the Docetaxel and the human serum albumin as described herein, and a therapeutically effective amount of at least one anti-cancer drug described herein.

In some embodiments, a composition comprising the Docetaxel and the human serum albumin as described herein and an anti-cancer drug are administered simultaneously.

In some embodiments, a composition comprising the Docetaxel and the human serum albumin as described herein and an anti-cancer drug are administered consecutively.

The composition comprising the Docetaxel and the human serum albumin described herein can be administered to an individual, such as human, via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of Docetaxel will be approximately those already employed in clinical therapies wherein Docetaxel is administered alone or in combination with other chemotherapeutic agents. Variation in dosage will likely occur depending on the condition being treated. Appropriate effective doses will also vary, as recognized by those skilled in the art, depending on the severity of the disease, the route of administration, the sex, age and general health condition of the subject, excipient usage, the possibility of co-usage with other therapeutic treatments such as use of other agents, and the judgment of the treating physician. For example, guidance for selecting an effective dose can be determined by reference to the prescribing information for Docetaxel.

Also, provided herein is a composition consisting essentially of Docetaxel and human serum albumin, wherein the Docetaxel and the human serum albumin in the composition have a ratio by weight from about 1:50 to about 1:1000. In some embodiments, the pH of the composition is neutral (e.g., pH of the composition is from about 5 to about 8, from about 5.5 to about 7.5, or from about 6 to about 7, or the pH of the composition is about 5, about 5.5, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, or about 8).

In some embodiments, the Docetaxel and the human serum albumin in the composition are in a ratio by weight from about 1:50 to about 1:500. In some embodiments, the Docetaxel and the human serum albumin in the composition are in a ratio by weight from about 1:60 to about 1:300. In some embodiments, the Docetaxel and the human serum albumin in the composition are in a ratio by weight from about 1:70 to about 1:250. In some embodiments, the Docetaxel and the human serum albumin in the composition are in a ratio by weight from about 1:80 to about 1:200. In some embodiments, the Docetaxel and the human serum albumin in the composition are in a ratio by weight from about 1:80 to about 1:150. In some embodiments, the Docetaxel and the human serum albumin in the composition are in a ratio by weight from about 1:90 to about 1:120. In some embodiments, the Docetaxel and the human serum albumin in the composition are in a ratio by weight from about 1:70 to about 1:1000. In some embodiments, the Docetaxel and the human serum albumin in the composition are in a ratio by weight from about 1:80 to about 1:1000. In some embodiments, the Docetaxel and the human serum albumin in the composition are in a ratio by weight from about 1:90 to about 1:1000. In some embodiments, the Docetaxel and the human serum albumin in the composition are in a ratio by weight from about 1:100 to about 1:1000. In some embodiments, the Docetaxel and the human serum albumin in the composition are in a ratio by weight from about 1:70 to about 1:500. In some embodiments, the Docetaxel and the human serum albumin in the composition are in a ratio by weight from about 1:80 to about 1:500. In some embodiments, the Docetaxel and the human serum albumin in the composition are in a ratio by weight from about 1:90 to about 1:500. In some embodiments, the Docetaxel and the human serum albumin in the composition are in a ratio by weight from about 1:100 to about 1:500. In some embodiments, the Docetaxel and the human serum albumin in the composition are in a ratio by weight of about 1:60, about 1:70, about 1:80, about 1:90, about 1:100, about 1:110, about 1:120, about 1:130, about 1:140, about 1:150, about 1:160, about 1:170, about 1:180, about 1:190, about 1:200, about 1:210, about 1:220, about 1:230, about 1:240, or about 1:250.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the Docetaxel can be a pharmaceutically acceptable salt of Docetaxel. In some embodiments, the Docetaxel can be a Docetaxel with three equivalents of the water solvate. In some embodiments, Docetaxel can be any one of crystal forms, amorphous forms, solvates and hydrates as described herein.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the composition is a clear aqueous solution for at least 3 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 24 hours when the composition is dissolved in an aqueous solution. In some embodiments, the composition is a clear aqueous solution for at least 3 days when the composition is dissolved in an aqueous solution. In some embodiments, the aqueous solution is substantially free of solvent other than water. In some embodiments, the aqueous solution free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution for at least 3 hours. In some embodiments, the aqueous formulation is a clear aqueous solution for at least 6 hours. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a clear aqueous solution for at least 3 days when dissolved in an aqueous solution at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is substantially free of solvent other than water. In some embodiments, the aqueous formulation is free of solvent other than water.

Also, provided herein is a pharmaceutical composition comprising the composition consisting essentially of the Docetaxel and the human serum albumin as described herein, and a pharmaceutically acceptable carrier.

Also, provided herein is a method of treating a cancer (e.g., any one of cancers described herein), the method comprising the step of administering to a subject in need thereof of a therapeutically effective amount of a pharmaceutical composition comprising the composition consisting essentially of the Docetaxel and the human serum albumin as described herein, and a pharmaceutically acceptable carrier.

In some embodiments, the cancer is any one of cancers described herein.

In some embodiments, the cancer is a solid tumor cancer. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma. In some embodiments, the cancer is a breast cancer. In some embodiments, the cancer is a non-small cell lung cancer. In some embodiments, the cancer is a prostate cancer. In some embodiments, the cancer is a gastric cancer. In some embodiments, the cancer is a head and neck cancer. In some embodiments the cancer is an ovarian cancer. In some embodiments, the cancer is a pancreatic cancer. In some embodiments, the cancer is a Kaposi's sarcoma.

Kits

The present invention also includes pharmaceutical kits useful, for example, in the treatment or prevention of any one of diseases or disorders referred to herein, which include one or more containers containing a pharmaceutical composition comprising a composition of docetaxel and the human serum albumin as described herein. Such kits can further include, if desired, one or more of various conventional pharmaceutical kit components, such as, for example, containers with one or more pharmaceutically acceptable carriers (e.g., water, 0.9% saline, or 5% dextrose), additional containers, etc., as will be readily apparent to those skilled in the art. Instructions, either as inserts or as labels, indicating quantities of the components to be administered (e.g., dosage amounts as described herein), guidelines for administration, and/or guidelines for mixing the components, can also be included in the kit.

Methods of Making

Also, provided herein are several methods to prepare a composition comprising a non-covalently bound complex comprising the Docetaxel and the human serum albumin as described herein, a composition comprising the Docetaxel and the human serum albumin as described herein, or a composition consisting essentially of the Docetaxel and the human serum albumin as described herein.

In some embodiments, the present disclosure provides a method of preparing a composition comprising a non-covalently bound complex comprising Docetaxel and human serum albumin, wherein the molar ratio of Docetaxel and human serum albumin in the complex is from about 0.1:1 to about 5:1.

In some embodiments, the present disclosure provides a method of preparing a composition comprising Docetaxel and human serum albumin, wherein the molar ratio of Docetaxel and the human serum albumin in the composition is from about 0.1:1 to about 5:1.

In some embodiments, the present disclosure provides a method of preparing a composition comprising Docetaxel and human serum albumin, wherein the molar ratio of Docetaxel and the human serum albumin in the composition is from about 0.1:1 to about 5:1, wherein the composition forms a clear aqueous solution when the composition is dissolved in an aqueous solution, and wherein the solubility of the composition in the aqueous solution is at least 10 mg/ml.

In some embodiments, the present disclosure provides a method of preparing a composition comprising Docetaxel and human serum albumin, wherein the Docetaxel and the human serum albumin in the composition have a ratio by weight from about 1:50 to about 1:1000.

In some embodiments, the present disclosure provides a method of preparing a composition consisting essentially of Docetaxel and human serum albumin, wherein the Docetaxel and the human serum albumin in the composition have a ratio by weight from about 1:50 to about 1:1000.

In some embodiments, the method comprises mixing an organic solution of Docetaxel in a polar water-miscible organic solvent and a first aqueous solution containing human serum albumin to form a second aqueous solution, wherein the second aqueous solution is a clear aqueous solution.

In some embodiments, the method further comprises removing said polar water-miscible organic solvent and water from the second aqueous solution.

A non-limiting preferred method is as follows.
Formation of the Organic Solution In some embodiments, Docetaxel is dissolved in a polar organic solvent (e.g., an alcohol such as methanol, ethanol, isopropanol, and/or n-butanol; THF, CH$_3$CN; DMF; or mixtures thereof) to form an organic solution.

As used herein, the term "organic solution" refers to a solution wherein at least one solvent is a non-aqueous solvent and the weight % of the non-aqueous solvent in the mixture of solvents is at least 50%, at least 60%, at least 70% or at least 90%. In some embodiments, organic solution is a solution in which does not comprise water as a solvent.

In some embodiments, the terms "organic solvent" and "non-aqueous solvent" are used interchangeably and refer to a liquid comprising is at least 50%, at least 60%, at least 70%, at least 90%, or at least 95% of a solvent other than water.

The polar organic solvent is miscible in water. In some embodiments, the polar organic solvent is an alcohol. In some embodiments, the polar organic solvent is ethanol or methanol, or mixtures thereof. In some embodiments, the polar organic solvent can be ethanol. In some embodiments, the polar organic solvent is methanol.

In some embodiments, the amount of polar organic solvent is from about 0.005 mL to about 10 mL per 1 mg of Docetaxel. In some embodiments, the amount of polar organic solvent is from about 0.01 mL to about 5 mL per 1 mg of Docetaxel. In some embodiments, the amount of polar organic solvent is from about 0.05 mL to about 5 mL per 1 mg of Docetaxel. In some embodiments, the amount of polar organic solvent is from about 0.1 mL to about 2.0 mL per 1 mg of Docetaxel. In some embodiments, the amount of polar organic solvent is from about 0.4 mL to about 2.0 mL per 1 mg of Docetaxel. In some embodiments, the amount of polar organic solvent is from about 0.5 mL to about 1.7 mL per 1 mg of Docetaxel. In some embodiments, the amount of polar organic solvent is about 0.4 mL, about 0.5 mL, about 0.6 mL, about 0.7 mL, about 0.8 mL, about 1 mL, about 1.2 mL, about 1.25 mL, about 1.35 mL, about 1.4 mL, about 1.45 mL, about 1.5 mL, about 1.6 mL, about 1.7 mL, or about 2.0 mL per 1 mg of Docetaxel.

Formation of the First Aqueous Solution

In some embodiments, a defined amount of human serum albumin is dissolved in an amount of water to form a first aqueous solution.

In some embodiments, the amount of aqueous solvent (e.g., water, saline, dextrose solution, or a buffer (e.g., any one of buffers described herein)) to prepare the first aqueous solution is from about 1 mL to about 1000 L, from about 2 mL to about 100 L, from about 3 mL to about 10 L, from about 4 mL to about 1 L, from about 5 mL to about 200 mL, from about 6 mL to about 100 mL, from about 10 mL to about 90 mL, from about 4 mL to about 20 mL, or from about 10 mL to about 20 mL. In some embodiments, the amount of water to prepare the first aqueous solution is about 4 mL, about 4.5 mL, about 5 mL, about 6 mL, about 10 mL, about 16 mL, about 17 mL, about 90 mL, or about 100 mL.

In some embodiments, the amount of HSA prepare the first aqueous solution is from about 100 mg to about 500 kg, from about 150 mg to about 100 kg, from about 200 mg to about 10 kg, from about 300 mg to about 500 g, from about 200 mg to about 100 g, or from about 200 mg to about 10 g. In some embodiments, the amount of HSA prepare the first aqueous solution is about 100 mg, about 200 mg, about 300 mg, about 600 mg, about 700 mg, about 800 mg, about 850 mg, about 900 mg, about 4500 mg, or about 5000 mg.

In some embodiments, the amount of aqueous solvent in the first aqueous solution is from about 0.01 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent in the first aqueous solution about 0.02 mL per 1 mg of human serum albumin.

In some embodiments, the resulting composition comprising the Docetaxel and the human serum albumin can have any molar ratio or any ratio by weight of the Docetaxel to the human serum albumin as described herein. In some embodiments, the human serum albumin is a fatty acid free human serum albumin. In some embodiments, the human serum albumin is essentially fatty acid free.

In some embodiments, the preparation of the organic solution and the preparation of the first aqueous solution are performed concurrently.

In some embodiments, the preparation of the organic solution and the preparation of the first aqueous solution are performed sequentially. In some embodiments, the preparation of the organic solution is performed before the preparation of the first aqueous solution. In some embodiments, the preparation of the first aqueous solution is performed before the preparation of the organic solution.

In some embodiments, the range of pH in the first aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the first aqueous solution is about 4, about 5, about 6, about 6.4, about 6.5, about 6.6, about 6.7, about 6.8, about 6.9, about 7, about 7.1, about 7.5, or about 8.

Formation of the Second Aqueous Solution

In some embodiments, the organic solution of Docetaxel is mixed with the first aqueous solution of human serum albumin to form a second aqueous solution. In some embodiments, the second aqueous solution is a clear aqueous solution.

In some embodiments, the volume ratio of the amount of water to the amount of the polar organic solvent is in a range from about 1:1 to about 1000:1. In some embodiments, the volume ratio of the amount of water to the amount of the polar organic solvent is in a range from about 1.5:1 to about 100:1. In some embodiments, the volume ratio of the amount of water to the amount of the polar organic solvent is in a range from about 1.5:1 to about 20:1. In some embodiments, the volume ratio of the amount of water to the amount of the polar organic solvent is in a range from about 1.5:1 to about 10:1. In some embodiments, the volume ratio of the amount of water to the amount of the polar organic solvent is in a range from about 2:1 to about 10:1. In some embodiments, the volume ratio of the amount of water to the amount of the polar organic solvent is about 1.5:1, about 2:1, about 2.2:1, about 2.3:1, about 2.4:1, about 2.5:1, about 3:1, about 4:1, about 5:1, about 6:1, about 7:1, about 8:1, about 9:1, or about 10:1.

In some embodiments, the organic solution is added to the first aqueous solution to form a second aqueous solution. In some embodiments, the organic solution is added dropwise to the first aqueous solution to form a second aqueous solution. In some embodiments, the first aqueous solution is added to the organic solution to form a second aqueous solution. In some embodiments, the mixing is performed with agitation. In some embodiments, the mixing is performed with stirring. In some embodiments, the mixing is performed with shaking.

In some embodiments, the addition is done at the temperature from about 0° C. to about 35° C. In some embodiments, the addition is done at the temperature from about 0° C. to about 25° C. In some embodiments, the addition is done at the temperature from about 0° C. to about 10° C. In some embodiments, the addition is done at the temperature from about 0° C. to about 5° C. In some embodiments, the addition is done at the temperature about 0° C. In some embodiments, the addition is done at the temperature about 5° C. In some embodiments, the addition is done at the temperature about 10° C.

In some embodiments, the time of addition is in a range from about 0.1 min to about 24 hours. In some embodiments, the time of addition is in a range from about 1 min to about 2 hour. In some embodiments, the time of addition is in a range from about 1 min to about 1 hour. In some embodiments, the time of addition is in a range from about 5 min to about 30 min.

In some embodiments, the range of pH in the second aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the second aqueous solution is about 4, about 5, about 6, about 6.4, about 6.5, about 6.6, about 6.7, about 6.8, about 6.9, about 7, about 7.1, about 7.5, or about 8.

Removal of Organic Solvent

In some embodiments, upon completion of mixing of the organic solution with the first aqueous solution to form the second aqueous solution, the polar organic solvent is removed from the second aqueous solution.

In some embodiments, the polar organic solvent is removed under reduced pressure. In some embodiments, the polar organic solvent is removed using rotary evaporation. In some embodiments, the polar organic solvent is removed under a vacuum.

In some embodiments, the removal of the polar organic solvent yields a clear aqueous solution. In some embodiments, water is removed from the aqueous under a vacuum. In some embodiments, water is removed from the aqueous solution using rotary evaporation. In some embodiments, water is removed from the aqueous solution by lyophilization.

In some embodiments, the solvents including both water and organic solvent are removed from the second aqueous solution simultaneously to provide a solid composition. In some embodiments, the solvents are removed under a vacuum. In some embodiments, the solvents are removed using rotary evaporation. In some embodiments, the solvents are removed by lyophilization. In some embodiments, the second aqueous solution was filtered before removal of the solvents.

Removal of Water from the Second Aqueous Solution

In some embodiments, upon removal of the organic solvent from the second aqueous solution, the water can be removed from the second aqueous solution to provide a solid.

In some embodiments, the second aqueous solution is filtered before removal of water. For example, the second aqueous solution can be filtered by a 0.22 micron filter before removal of water.

As used herein, the term "micron" refers to a unit of measure of one one-thousandth of a millimeter.

In some embodiments, the water is removed under a vacuum. In some embodiments, the water is removed using rotary evaporation. In some embodiments, the water is removed by lyophilization.

In some embodiments, the amount of docetaxel that is bound to the HSA (e.g., non-covalently) in the solid composition comprising the composition comprising docetaxel and HSA (as described herein) is at least 40%, at least 50%, at least 60%, at least 70%, at least 80%, at least 90%, at least 95%, at least 99%, or about 100% of the total about of docetaxel in the solid composition.

Reconstitution of the Solid

In some embodiments the solid composition comprising the Docetaxel and the human serum albumin (e.g., the solid composition prepared by removing organic solvent from the second aqueous solution and removing water from the second aqueous solution) is mixed with a water solution. In some embodiments, the water solution is a saline solution. In some embodiments, the water solution is a 5% Dextrose water solution. In some embodiments, the mixing is the addition of the water solution to the solid. In some embodiments, the mixing is the addition of the solid to the water solution. In some embodiments, the mixing reconstitutes the solid. In some embodiments, the mixing yields a clear aqueous solution. In some embodiments, the range of pH in the reconstituted solution is from about 5 to about 8, from about 5 to about 7, from about 6 to about 7, from about 6.5 to about 7.5, from about 4 to about 6, or from about 6 to about 6.5. In some embodiments, the pH of the reconstituted solution is about 5, about 6, about 6.4, about 6.5, about 6.6, about 6.7, about 6.8, about 6.9, about 7, about 7.1, about 7.5, or about 8.

Unless otherwise defined, all technical and scientific terms used herein have the same meaning as commonly understood by one of ordinary skill in the art to which this disclosure belongs. Methods and materials are described herein for use in the present disclosure; other suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Composition Prepared by the Process

In some embodiments, the present disclosure provides a composition comprising docetaxel and human serum albumin, wherein the weight ratio of docetaxel and the human serum albumin in the composition is from about 1:50 to about 1:1000, produced by a method comprising the steps of:

(i) obtaining an organic solution of docetaxel in a polar water-miscible organic solvent;

(ii) obtaining a first aqueous solution of human serum albumin; and (iii) mixing the organic solution of docetaxel and the first aqueous solution of human serum albumin to obtain a second aqueous solution comprising the composition comprising docetaxel and human serum albumin.

In some embodiments, the range of pH in the first aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the first aqueous solution is about 4, about 5, about 6, about 6.4, about 6.5, about 6.6, about 6.7, about 6.8, about 6.9, about 7, about 7.1, about 7.5, or about 8.

In some embodiments, the range of pH in the second aqueous solution is from about 3 to about 9, from about 4 to about 8, from about 5 to about 8, from about 5 to about 7, from about 6 to about 7, from about 3 to about 5, from about 3 to about 7, from about 4 to about 6, or from about 6 to about 6.5. In some embodiments, the pH of the second aqueous solution is about 4, about 5, about 6, about 6.4, about 6.5, about 6.6, about 6.7, about 6.8, about 6.9, about 7, about 7.1, about 7.5, or about 8.

In some embodiments, the Docetaxel and the human serum albumin in the composition are in a ratio by weight from about 1:50 to about 1:500. In some embodiments, the Docetaxel and the human serum albumin in the composition are in a ratio by weight from about 1:60 to about 1:300. In some embodiments, the Docetaxel and the human serum albumin in the composition are in a ratio by weight from about 1:70 to about 1:250. In some embodiments, the Docetaxel and the human serum albumin in the composition are in a ratio by weight from about 1:80 to about 1:200. In some embodiments, the Docetaxel and the human serum albumin in the composition are in a ratio by weight from about 1:90 to about 1:120. In some embodiments, the Docetaxel and the human serum albumin in the composition are in a ratio by weight from about 1:70 to about 1:1000. In some embodiments, the Docetaxel and the human serum albumin in the composition are in a ratio by weight from about 1:80 to about 1:1000. In some embodiments, the Docetaxel and the human serum albumin in the composition are in a ratio by weight from about 1:90 to about 1:1000. In some embodiments, the Docetaxel and the human serum albumin in the composition are in a ratio by weight from about 1:100 to about 1:1000. In some embodiments, the Docetaxel and the human serum albumin in the composition are in a ratio by weight from about 1:70 to about 1:500. In some embodiments, the Docetaxel and the human serum albumin in the composition are in a ratio by weight from about 1:80 to about 1:500. In some embodiments, the Docetaxel and the human serum albumin in the composition are in a ratio by weight from about 1:90 to about 1:500. In some embodiments, the Docetaxel and the human serum albumin in the composition are in a ratio by weight from about 1:100 to about 1:500. In some embodiments, the Docetaxel and the human serum albumin in the composition are in a ratio by weight of about 1:60, about 1:70, about 1:80, about 1:90, about 1:100, about 1:110, about 1:120, about 1:130, about 1:140, about 1:150, about 1:160, about 1:170, about 1:180, about 1:190, about 1:200, about 1:210, about 1:220, about 1:230, about 1:240, or about 1:250.

In some embodiments, the docetaxel can be a pharmaceutically acceptable salt of Docetaxel. In some embodiments, the docetaxel can be a docetaxel with three equivalents of the water solvate. In some embodiments, docetaxel can be any one of crystal forms, amorphous forms, solvates and hydrates as described herein.

In some embodiments, the human serum albumin is essentially fatty acid free.

In some embodiments, the composition comprises a non-covalently bound complex comprising docetaxel and human serum albumin.

In some embodiments, the amount of the polar water-miscible organic solvent in the organic solution is from about 0.01 mL to about 5 mL per 1 mg of docetaxel.

In some embodiments, the amount of the polar water-miscible organic solvent in the organic solution is from about from about 0.1 mL to about 2.0 mL per 1 mg of docetaxel.

In some embodiments, the amount of the polar water-miscible organic solvent in the organic solution is from about 0.4 mL to about 2.0 mL per 1 mg of docetaxel.

In some embodiments, the amount of the polar water-miscible organic solvent in the organic solution is from about 0.5 mL to about 1.7 mL per 1 mg of docetaxel.

In some embodiments, the amount of organic solvent is from about 0.005 mL to about 10 mL per 1 mg of Docetaxel. In some embodiments, the amount of organic solvent is from about 0.01 mL to about 5 mL per 1 mg of Docetaxel. In some embodiments, the amount of organic solvent is from about 0.05 mL to about 5 mL per 1 mg of Docetaxel. In some embodiments, the amount of organic solvent is from about 0.1 mL to about 2.0 mL per 1 mg of Docetaxel. In some embodiments, the amount of organic solvent is from about 0.4 mL to about 2.0 mL per 1 mg of Docetaxel. In some embodiments, the amount of organic solvent is from about 0.5 mL to about 1.7 mL per 1 mg of Docetaxel. In some embodiments, the amount of organic solvent is about 0.4 mL, about 0.5 mL, about 0.6 mL, about 0.7 mL, about 0.8 mL, about 1 mL, about 1.2 mL, about 1.25 mL, about 1.35 mL, about 1.4 mL, about 1.45 mL, about 1.5 mL, about 1.6 mL, about 1.7 mL, or about 2.0 mL per 1 mg of Docetaxel.

In some embodiments, the amount of aqueous solvent in the first aqueous solution is from about 0.005 mL to about 0.05 mL per 1 mg of human serum albumin.

In some embodiments, the amount of aqueous solvent in the first aqueous solution is from about 0.01 mL to about 0.05 mL per 1 mg of human serum albumin.

In some embodiments, the amount of aqueous solvent in the first aqueous solution is from about 0.015 mL to about 0.04 mL per 1 mg of human serum albumin.

In some embodiments, the amount of aqueous solvent in the first aqueous solution is from about 0.01 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent in the first aqueous solution about 0.02 mL per 1 mg of human serum albumin.

In some embodiments, the polar water-miscible organic solvent is an alcohol selected from the group consisting of methanol, ethanol, isopropanol, n-butanol, and mixtures thereof.

In some embodiments, the polar water-miscible organic solvent is selected from methanol, ethanol, and mixtures thereof.

In some embodiments, the polar water-miscible organic solvent is methanol.

In some embodiments, the aqueous solvent is water.

In some embodiments, the mixing comprises adding the organic solution to the first aqueous solution. In some embodiments, wherein the mixing comprises adding the first aqueous solution to the organic solution. In some embodiments, the adding is carried out dropwise. In some embodiments, the adding is carried out for a period of time from several minutes to several hours. In some embodiments, the adding is carried out for a period of time from 2 min to 24 hours. In some embodiments, the adding is carried out for a period of time from 2 min minutes to 12 hours, from 2 min to 6 hours, from 3 min to 3 hours, from 2 min to 1 hour, from 2 min to 30 min, or from 2 min to 25 min.

In some embodiments, the mixing is carried out at a temperature from about 0° C. to about 25° C. In some embodiments, mixing is carried out at ambient temperature (e.g., about 25° C.). In some embodiments, the mixing is carried out at a temperature from about 0° C. to about 5° C. In some embodiments, the mixing is carried out at about 0° C.

In some embodiments, the volume ratio of the amount of aqueous solvent to the amount of the organic solvent in the second aqueous solution is in a range from about 1:1 to about 1000:1. In some embodiments, the volume ratio of the amount of aqueous solvent to the amount of the organic solvent in the second aqueous solution is in a range from about 1.5:1 to about 100:1. In some embodiments, the volume ratio of the amount of aqueous solvent to the amount of the organic solvent in the second aqueous solution is in a range from about 1.5:1 to about 20:1. In some embodiments, the volume ratio of the amount of aqueous solvent to the amount of the organic solvent in the second aqueous solution is in a range from about 1.5:1 to about 10:1. In some embodiments, the volume ratio of the amount of aqueous solvent to the amount of the organic solvent in the second aqueous solution is in a range from about 2:1 to about 10:1. In some embodiments, the volume ratio of the amount of aqueous solvent to the amount of the organic solvent in the second aqueous solution is about 1.5:1, about 2:1, about 2.2:1, about 2.3:1, about 2.4:1, about 2.5:1, about 3:1, about 4:1, about 5:1, about 6:1, about 7:1, about 8:1, about 9:1, or about 10:1. In some embodiments, the aqueous solvent is water. In some embodiments, the aqueous solvent is water and the organic solvent is an alcohol. In some embodiments, the aqueous solvent is water and the organic solvent is methanol.

In some embodiments, the composition is prepared by further comprising the step of removing the polar water-miscible organic solvent from the second aqueous solution to obtain a third aqueous solution comprising the composition comprising docetaxel and human serum albumin. In some embodiments, the composition is prepared by further comprising the step of removing aqueous solvent from the third aqueous solution to obtain the composition comprising docetaxel and human serum albumin.

In some embodiments, the composition is prepared by further comprising the step of removing the organic solvent (e.g. methanol) and the aqueous solvent (e.g., water) from the second aqueous solution to obtain the composition comprising docetaxel and human serum albumin.

In some embodiments, the removing as carried out in vacuum (e.g., using the rotovap). In some embodiments, the removing is carried out by lyophilization.

In some embodiments, the composition forms a clear aqueous solution when the composition is dissolved in an aqueous solvent, and wherein the solubility of the composition in the aqueous solution is at least 10 mg/ml.

In some embodiments, the composition is a solid formulation

In some embodiments, the composition is an aqueous formulation. In some embodiments, the aqueous formulation is substantially free of solvent other than water. In some embodiments, the aqueous formulation is free of a surfactant. In some embodiments, the surfactant is selected from the group consisting of CREMOPHOR® surfactants and Polysorbate 80. In some embodiments, the aqueous formulation is a clear aqueous solution. In some embodiments, the aqueous formulation is a clear aqueous solution for at least 2 hours, at least 4 hours, at least 6 hours, at least 8 hours, at least 24 hours, at least 48 hours, or at least 72 hours.

In some embodiments, the present disclosure provides a pharmaceutical composition comprising the composition as prepared by a process as described herein, and a pharmaceutically acceptable carrier.

In some embodiments, the present disclosure provides a method of treating a cancer, the method comprising the step of administering to a subject in need thereof a therapeutically effective amount of the pharmaceutical composition as described herein.

In some embodiments, the cancer is a solid tumor. In some embodiments, the cancer is selected from the group consisting of breast cancer, non-small cell lung cancer, prostate cancer, gastric cancer, head and neck cancer, ovarian cancer, pancreatic cancer, and Kaposi's sarcoma.

EXAMPLES

Materials and Methods
HPLC Analysis:

The HPLC system used herein is a SHIMADZU LC-10AT vp series system, which consists of a SHIMADZU LC-10AT vp pump, a manual injector, a SHIMADZU CTO-10AS vp column oven, a SHIMADZU SPD-10A vp wavelength detector, and a SHIMADZU LC solution workstation. Waters XTERRA RP10 column (4.6 mm×150 mm, 5 µm) is used as an analytical HPLC column. The column oven temperature is 30° C. Mobile phase is composed of methanol and water (70:30, v/v) and pumped at a flow rate of 1 ml/minute. The effluent is detected at a wavelength of 233 nm using a UV detector. The sample injection amount is 20 µl.

Example 1: Composition Comprising Docetaxel and Human Serum Albumin (HSA)

The Molar Ratio of Docetaxel to HSA Prepared was about 1:1.

Docetaxel (10 mg) was dissolved in methanol (10 ml) in a flask to give a clear solution. HSA (824 mg) (native fatty acid free human serum albumin purchased from SeraCare Life Sciences, product code: HS-455-80, which contains fatty acids <0.2 mg/gm) as a powder was dissolved in 20 ml of water in a round bottom flask. The methanol solution of Docetaxel was added slowly dropwise into the flask of the HSA solution with rapid stirring. The addition took about 25 minutes to complete. Upon completion of the addition, a clear solution was obtained. The methanol was removed under vacuum until the volume of the solution was about 18 ml to give a clear solution. The resulting aqueous water solution was lyophilized overnight to give a white solid.

A sample of 50 mg of the lyophilized solid was reconstituted by adding 1 mL water to give a clear solution. This clear water solution stays clear after 24 hours without any solid precipitation.

A sample of 50 mg of the lyophilized solid was reconstituted by adding 1 mL 2% ethanol water solution (2% ethanol in water) to give a clear solution. This 2% ethanol water solution stays clear after 24 hours without any solid precipitation.

Example 2: Composition Comprising Docetaxel and Human Serum Albumin (HSA)

The Molar Ratio of Docetaxel to HSA Prepared was about 1.3:1.

Docetaxel (3 mg) was dissolved in methanol (3 ml) in a glass vial to give a clear solution. HSA (190 mg) (native fatty acid free human serum albumin purchased from Sera-Care Life Sciences, product code: HS-455-80, which contains fatty acids <0.2 mg/gm) as a powder was dissolved in 6 ml of water in a round bottom flask. The methanol solution of Docetaxel was added slowly dropwise into the flask of the HSA solution with rapid stirring. The addition took about 8 minutes to complete. Upon completion of the addition, a clear solution was obtained. The methanol was removed under vacuum until the volume of the solution was about 5 ml to give a clear solution. The resulting aqueous solution was lyophilized overnight to give a white solid.

A sample of 50 mg of the lyophilized solid was reconstituted by adding 1 mL water to give a clear solution. This clear water solution stays clear without any solid precipitation after 24 hours at room temperature.

Example 3: Composition Comprising Docetaxel and Human Serum Albumin (HSA)

The Molar Ratio of Docetaxel to HSA Prepared was about 1.5:1.

Docetaxel (3 mg) was dissolved in methanol (3 ml) in a glass vial to give a clear solution. HSA (165 mg) (native fatty acid free human serum albumin purchased from Sera-Care Life Sciences, product code: HS-455-80, which contains fatty acids <0.2 mg/gm) as a powder was dissolved in 6 ml of water in a round bottom flask. The methanol solution of Docetaxel was added slowly dropwise into the flask of the HSA solution with rapid stirring. The addition took about 8 minutes to complete. Upon completion of the addition, a clear solution was obtained. The methanol was removed under vacuum until the volume of the solution was about 5 ml to give a clear solution. The resulting aqueous water solution was lyophilized overnight to give a white solid.

A sample of 50 mg of the lyophilized solid was reconstituted by adding 1 mL water to give a slightly cloudy solution.

Example 4: Composition Comprising Docetaxel and Human Serum Albumin (HSA)

The Molar Ratio of Docetaxel to HSA Prepared was about 1.2:1.

Docetaxel (10 mg) was dissolved in methanol (5 ml) in a glass vial to give a clear solution. HSA (687 mg) (native fatty acid free human serum albumin purchased from Sera-Care Life Sciences, product code: HS-455-80, which contains fatty acids <0.2 mg/gm) as a powder was dissolved in 15 ml of water in a round bottom flask. The methanol solution of Docetaxel was added slowly dropwise into the flask of the HSA solution with rapid stirring. The addition took about 15 minutes to complete. Upon completion of the addition, a clear solution was obtained. The methanol was removed under vacuum until the volume of the solution was about 13 ml to give a clear solution. The clear water solution was filtered by a 0.22 micron aqueous phase filter. The resulting clear aqueous solution was lyophilized overnight to give a white solid.

A sample of 50 mg of the lyophilized solid was reconstituted by adding 1 mL water to give a clear solution. This clear water solution stays clear with no precipitation of Docetaxel after 6 hours at room temperature. This clear water solution stays clear with no precipitation of Docetaxel after 24 hours at room temperature. This clear water solution stays clear with no precipitation of Docetaxel after 3 days at room temperature.

A sample of 70 mg of the lyophilized solid was reconstituted by adding 1 mL water to give a clear solution. This clear water solution stays clear with no precipitation of Docetaxel after 6 hours at room temperature. This clear water solution stays clear with no precipitation of Docetaxel after 24 hours at room temperature. This clear water solution stays clear with no precipitation of Docetaxel after 3 days at room temperature.

A sample of 50 mg of the lyophilized solid was reconstituted by adding 1 mL water to give a clear solution. This clear water solution stays clear with no precipitation of Docetaxel after 6 hours at 4° C. This clear water solution stays clear with no precipitation of Docetaxel after 24 hours at 4° C. This clear water solution stays clear with no precipitation of Docetaxel after 3 days at 4° C.

A sample of 50 mg of the lyophilized solid was reconstituted by adding 1 mL saline to give a clear solution. This clear saline solution stays clear with no precipitation of Docetaxel after 6 hours at room temperature. This clear saline solution stays clear with no precipitation of Docetaxel after 24 hours at room temperature. This clear saline solution stays clear with no precipitation of Docetaxel after 3 days at room temperature.

Example 5: Composition Comprising Docetaxel and Human Serum Albumin (HSA)

The Molar Ratio of Docetaxel to HSA Prepared was about 1.2:1.

Docetaxel (3 mg) was dissolved in methanol (1.5 ml) in a glass vial to give a clear solution. HSA (206 mg) (native fatty acid free human serum albumin purchased from Sera-Care Life Sciences, product code: HS-455-80, which contains fatty acids <0.2 mg/gm) as a powder was dissolved in 4.5 ml of water in a round bottom flask. The methanol solution of Docetaxel was added slowly dropwise into the flask of the HSA solution with rapid stirring. The addition took about 4 minutes to complete. Upon completion of the addition, a clear solution was obtained. The clear solution was filtered by a 0.22 micron aqueous phase filter. The resulting clear aqueous solution with methanol was directly lyophilized overnight to give a white solid.

A sample of 50 mg of the lyophilized solid was reconstituted by adding 1 mL water to give a clear solution. This clear water solution stays clear with no precipitation of Docetaxel after 6 hours at room temperature. This clear water solution stays clear with no precipitation of Docetaxel after 24 hours at room temperature. This clear water solution stays clear with no precipitation of Docetaxel after 3 days at room temperature.

Example 6: Composition Comprising Docetaxel and Human Serum Albumin (HSA)

The Molar Ratio of Docetaxel to HSA Prepared was about 0.5:1.

Docetaxel (2 mg) was dissolved in methanol (1 ml) in a glass vial to give a clear solution. HSA (329 mg) (native fatty acid free human serum albumin purchased from Sera-Care Life Sciences, product code: HS-455-80, which contains fatty acids <0.2 mg/gm) as a powder was dissolved in 6 ml of water in a round bottom flask. The methanol solution of Docetaxel was added slowly dropwise into the flask of the HSA solution with rapid stirring. The addition took about 2-3 minutes to complete. Upon completion of the addition, a clear solution was obtained. The methanol was removed under vacuum until the volume of the solution was about 5 ml to give a clear solution. The clear water solution was filtered by a 0.22 micron aqueous phase filter. The resulting clear aqueous solution was lyophilized overnight to give a white solid.

A sample of 50 mg of the lyophilized solid was reconstituted by adding 1 mL water to give a clear solution. This clear water solution stays clear with no precipitation of Docetaxel after 6 hours at room temperature. This clear water solution stays clear with no precipitation of Docetaxel after 24 hours at room temperature. This clear water solution stays clear with no precipitation of Docetaxel after 3 days at room temperature.

Example 7: Composition Comprising Docetaxel and Human Serum Albumin (Recombinant Human Serum Albumin The Molar Ratio of Docetaxel to Recombinant Human Serum Albumin Prepared was about 1:1.

Docetaxel (10 mg) was dissolved in methanol (7 ml) in a glass vial to give a clear solution. Recombinant human serum albumin (823 mg) (fatty acid free recombinant human serum albumin (no fatty acids detected) purchased from Wuhan Healthgen Biotechnology Corp., www.oryzogen.com) as a powder was dissolved in 16 ml of water in a round bottom flask. The methanol solution of Docetaxel was added slowly dropwise into the flask of the recombinant human serum albumin solution with rapid stirring. Upon completion of the addition, a clear solution was obtained. The methanol was removed under vacuum until the volume of the solution was about 14 ml to give a clear solution. The clear water solution was filtered by a 0.22 micron aqueous phase filter. The resulting clear aqueous solution was lyophilized overnight to give a white solid.

A sample of 50 mg of the lyophilized solid was reconstituted by adding 1 mL water to give a clear solution. This clear water solution stays clear with no precipitation of Docetaxel after 6 hours at room temperature. This clear water solution stays clear with no precipitation of Docetaxel after 24 hours at room temperature. This clear water solution stays clear with no precipitation of Docetaxel after 3 days at room temperature.

Example 8: Composition Comprising Docetaxel and Human Serum Albumin (HSA)

The Ratio by Weight of Docetaxel to HSA Prepared was about 1:85.

Docetaxel (10 mg) was dissolved in methanol (7 ml) in a glass vial to give a clear solution. HSA (850 mg) (native fatty acid free human serum albumin purchased from Sera-Care Life Sciences, product code: HS-455-80, which contains fatty acids <0.2 mg/gm) as a powder was dissolved in 17 ml of water in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution. This clear water solution stays clear with no precipitation of Docetaxel after 6 hours at room temperature. This clear water solution stays clear with no precipitation of Docetaxel after 24 hours at room temperature.

Example 9: Composition Comprising Docetaxel and Human Serum Albumin (HSA)

The Ratio by Weight of Docetaxel to HSA Prepared was about 1:90.

Docetaxel (50 mg) was dissolved in methanol (30 ml) in a glass vial to give a clear solution. HSA (4500 mg) (native fatty acid free human serum albumin purchased from Sera-Care Life Sciences, product code: HS-455-80, which contains fatty acids <0.2 mg/gm) as a powder was dissolved in 90 ml of water in a round bottom flask. The methanol solution of Docetaxel was added slowly dropwise into the flask of the HSA solution with rapid stirring at 0° C. Upon completion of the addition, a clear solution was obtained. Additional 8.5 ml of methanol was added into the solution. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution. This clear water solution stays clear with no precipitation of Docetaxel after 6 hours at room temperature. This clear water solution stays clear with no precipitation of Docetaxel after 24 hours at room temperature.

Example 10: Composition Comprising Docetaxel and Human Serum Albumin (HSA)

The Ratio by Weight of Docetaxel to HSA Prepared was about 1:100.

Docetaxel (50 mg) was dissolved in methanol (30 ml) in a glass vial to give a clear solution. HSA (5000 mg) (native fatty acid free human serum albumin purchased from Sera-Care Life Sciences, product code: HS-455-80, which contains fatty acids <0.2 mg/gm) as a powder was dissolved in 100 ml of water in a round bottom flask. The methanol solution of Docetaxel was added slowly dropwise into the flask of the HSA solution with rapid stirring at 0° C. Upon completion of the addition, a clear solution was obtained. Additional 13 ml of methanol was added into the solution. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution. This clear water solution stays clear with no precipitation of Docetaxel after 6 hours at room temperature. This clear water solution stays clear with no precipitation of Docetaxel after 24 hours at room temperature.

Example 11: Composition Comprising Docetaxel and Human Serum Albumin (HSA)

The Ratio by Weight of Docetaxel to HSA Prepared was about 1:100.

Docetaxel (5 mg) was dissolved in methanol (4.3 ml) in a glass vial to give a clear solution. HSA (500 mg) (native fatty acid free human serum albumin purchased from Golden West Biologicals, Inc., CAT #: HA1020) as a powder was dissolved in 10 ml of water in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution. This clear water solution stays clear with no precipitation of Docetaxel after 3 hours at room temperature. This clear water solution stays clear with no precipitation of Docetaxel after 6 hours at room temperature. This clear water solution stays clear with no precipitation of Docetaxel after 24 hours at room temperature.

Example 12: Composition Comprising Docetaxel and Human Serum Albumin (HSA)

The Ratio by Weight of Docetaxel to HSA Prepared was about 1:200.

Docetaxel (1 mg) was dissolved in methanol (1.7 ml) in a glass vial to give a clear solution. HSA (200 mg) (native human serum albumin purchased from Golden West Biologicals, Inc., CAT #: HA1000) as a powder was dissolved in 4 ml of water in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution with no precipitation of Docetaxel.

Example 13: Composition Comprising Docetaxel and Human Serum Albumin (HSA)

The Ratio by Weight of Docetaxel to HSA Prepared was about 1:150.

Docetaxel (1 mg) was dissolved in methanol (1 ml) in a glass vial to give a clear solution. HSA (150 mg) (native human serum albumin purchased from Golden West Biologicals, Inc., CAT #: HA1000) as a powder was dissolved in 3 ml of water in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution with no precipitation of Docetaxel.

Example 14: Composition Comprising Docetaxel and Human Serum Albumin (HSA)

The Ratio by Weight of Docetaxel to HSA Prepared was about 1:150.

Docetaxel (2 mg) was dissolved in methanol (2.5 ml) in a glass vial to give a clear solution. A solution of HSA (300 mg, 1.5 ml) (20% human serum albumin solution for infusion (product name: AlbuRx) from CSL Behring) was added into 4.5 ml of water to give a HSA solution (6 ml) in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 15: Composition Comprising Docetaxel and Human Serum Albumin (HSA)

The Ratio by Weight of Docetaxel to HSA Prepared was about 1:160.

Docetaxel (2 mg) was dissolved in methanol (2.7 ml) in a glass vial to give a clear solution. A solution of HSA (320 mg, 1.6 ml) (20% human serum albumin solution for infusion (product name: AlbuRx) from CSL Behring) was added into 4.8 ml of water to give a HSA solution (6.4 ml) in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 16: Composition Comprising Docetaxel and Human Serum Albumin (HSA)

The Ratio by Weight of Docetaxel to HSA Prepared was about 1:170.

Docetaxel (2 mg) was dissolved in methanol (2.9 ml) in a glass vial to give a clear solution. A solution of HSA (340 mg, 1.7 ml) (20% human serum albumin solution for infusion (product name: AlbuRx) from CSL Behring) was added into 5.1 ml of water to give a HSA solution (6.8 ml) in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 17: Composition Comprising Docetaxel and Human Serum Albumin (HSA)

The Ratio by Weight of Docetaxel to HSA Prepared was about 1:180.

Docetaxel (2 mg) was dissolved in methanol (3.1 ml) in a glass vial to give a clear solution. A solution of HSA (360 mg, 1.8 ml) (20% human serum albumin solution for infusion (product name: AlbuRx) from CSL Behring) was added into 5.4 ml of water to give a HSA solution (7.2 ml) in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 18: Composition Comprising Docetaxel and Human Serum Albumin (HSA)

The Ratio by Weight of Docetaxel to HSA Prepared was about 1:200.

Docetaxel (2 mg) was dissolved in methanol (3.4 ml) in a glass vial to give a clear solution. A solution of HSA (400 mg, 2 ml) (20% human serum albumin solution for infusion (product name: AlbuRx) from CSL Behring) was added into 6 ml of water to give a HSA solution (8 ml) in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear water solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 19: Measure the Correlation Between HPLC Peak Area and the Docetaxel Concentration Methanol solutions of Docetaxel in 7 different concentrations, 0.025 mg/ml, 0.05 mg/ml, 0.075 mg/ml, 0.1 mg/ml, 0.15 mg/ml, 0.2 mg/ml and 0.25 mg/ml, were prepared. The 7 Docetaxel methanol solutions were analyzed in HPLC. The peak area and concentration of Docetaxel were correlated using linear regression. The linear regression data is shown as below.

$$Y \text{ (peak area)} = 61390 + 2.571E7*X \text{ (concentration)},$$
$$R = 0.9999, P < 0.0001.$$

Example 20: Measure the Docetaxel Concentrations in the Clear Aqueous Solutions Before and after the Filtration at 0 Hour, and after the Filtration at 2 Hour, 4 Hour, 6 Hour, 8 Hour, 24 Hour, 48 Hour, and 72 Hour 2.5 g of the lyophilized solid of the composition comprising Doectaxel and HSA (the ratio by weight about 1:100) from Example 10 was dissolved in 50 ml of water to give a clear aqueous solution, which was kept at about 20° C. Immediately after the lyophilized solid was dissolved in water, 6 ml of the clear aqueous solution was taken out from the 50 ml solution. Then 1 ml of the solution was taken out from the 6 ml clear aqueous solution to give the solution DC-0-0h, and the remaining 5 ml of the solution was filtered by the same 0.22 micron aqueous phase filter at 1 ml at a time to give the solutions DC-1-0h, DC-2-0h, DC-3-0h, DC-4-0h, and DC-5-0h. To 200 µl of the solutions DC-0-0h and DC-5-0h were added 800 µl of acetonitrile separately. The mixtures were vortexed for seconds and then centrifuged at 4,000 g for 5 minutes. The supernatants were removed and collected followed by injection on HPLC. The same procedure was repeated 2 more times for each of solutions DC-0-0h and DC-5-0h. Based on the HPLC data and the measurement data of Example 19, the Docetaxel concentrations of the solutions of DC-0-0h, and DC-5-0h have been calculated and shown in the Table 1. At 0 hour, the Docetaxel concentration of the clear aqueous solution after the filtration was about 100.4% of the Docetaxel concentration of the clear aqueous solution before the filtration.

TABLE 1

| Solution Number | Docetaxel Concentration (mg/ml) | Average Docetaxel Concentration (mg/ml) |
| --- | --- | --- |
| DC-0-0h-1 | 0.4939 | 0.4908 |
| DC-0-0h-2 | 0.4902 | |
| DC-0-0h-3 | 0.4884 | |
| DC-5-0h-1 | 0.4964 | 0.4926 |
| DC-5-0h-2 | 0.4902 | |
| DC-5-0h-3 | 0.4913 | |

At 2 hour, 5 ml of the clear aqueous solution was taken out from the remaining 44 ml of the aqueous solution. Then 1 ml of the solution was taken out from the 5 ml clear aqueous solution and filtered by a 0.22 micron aqueous phase filter to give the solution DC-1-2h, and the remaining 4 ml of the solution was filtered by the same 0.22 micron aqueous phase filter at 1 ml at a time to give the solutions DC-2-2h, DC-3-2h, DC-4-2h, and DC-5-2h. To 200 µl of the solution DC-5-2h was added 800 µl of acetonitrile. The mixture was vortexed for seconds and then centrifuged at 4,000 g for 5 minutes. The supernatant was removed and collected followed by injection on HPLC. The same procedure was repeated 2 more times for the solution DC-5-2h. Based on the HPLC data and the measurement data of Example 19, the Docetaxel concentrations of the solution DC-5-2h have been calculated and shown in the Table 2. At 2 hour, the Docetaxel concentration of the clear aqueous solution after the filtration was about 100% of the Docetaxel concentration of the clear aqueous solution at 0 hour before the filtration.

TABLE 2

| Solution Number | Docetaxel Concentration (mg/ml) | Average Docetaxel Concentration (mg/ml) |
| --- | --- | --- |
| DC-5-2h-1 | 0.4898 | 0.4908 |
| DC-5-2h-2 | 0.4910 | |
| DC-5-2h-3 | 0.4916 | |

At 4 hour, 5 ml of the clear aqueous solution was taken out from the remaining 39 ml of the aqueous solution. The experiments were done for the 5 ml of the clear aqueous solution taken out at 4 hour using the same protocol as for the 5 ml of the clear aqueous solution taken out at 2 hour. Based on the HPLC data and the measurement data of Example 19, the Docetaxel concentrations of the solution DC-5-4h have been calculated and shown in the Table 3. At 4 hour, the Docetaxel concentration of the clear aqueous solution after the filtration was about 99.96% of the Docetaxel concentration of the clear aqueous solution at 0 hour before the filtration.

TABLE 3

| Solution Number | Docetaxel Concentration (mg/ml) | Average Docetaxel Concentration (mg/ml) |
| --- | --- | --- |
| DC-5-4h-1 | 0.4903 | 0.4906 |
| DC-5-4h-2 | 0.4913 | |
| DC-5-4h-3 | 0.4903 | |

At 6 hour, 5 ml of the clear aqueous solution was taken out from the remaining 34 ml of the aqueous solution. The experiments were done for the 5 ml of the clear aqueous solution taken out at 6 hour using the same protocol as for the 5 ml of the clear aqueous solution taken out at 2 hour. Based on the HPLC data and the measurement data of Example 19, the Docetaxel concentrations of the solution DC-5-6h have been calculated and shown in the Table 4. At 6 hour, the Docetaxel concentration of the clear aqueous solution after the filtration was about 99.84% of the Docetaxel concentration of the clear aqueous solution at 0 hour before the filtration.

TABLE 4

| Solution Number | Docetaxel Concentration (mg/ml) | Average Docetaxel Concentration (mg/ml) |
| --- | --- | --- |
| DC-5-6h-1 | 0.4899 | 0.4900 |
| DC-5-6h-2 | 0.4900 | |
| DC-5-6h-3 | 0.4900 | |

At 8 hour, 5 ml of the clear aqueous solution was taken out from the remaining 29 ml of the aqueous solution. The experiments were done for the 5 ml of the clear aqueous solution taken out at 8 hour using the same protocol as for the 5 ml of the clear aqueous solution taken out at 2 hour. Based on the HPLC data and the measurement data of Example 19, the Docetaxel concentrations of the solution DC-5-8h have been calculated and shown in the Table 5. At 8 hour, the Docetaxel concentration of the clear aqueous solution after the filtration was about 99.27% of the Docetaxel concentration of the clear aqueous solution at 0 hour before the filtration.

TABLE 5

| Solution Number | Docetaxel Concentration (mg/ml) | Average Docetaxel Concentration (mg/ml) |
|---|---|---|
| DC-5-8h-1 | 0.4856 | 0.4872 |
| DC-5-8h-2 | 0.4879 | |
| DC-5-8h-3 | 0.4882 | |

At 24 hour, 5 ml of the clear aqueous solution was taken out from the remaining 24 ml of the aqueous solution. The experiments were done for the 5 ml of the clear aqueous solution taken out at 24 hour using the same protocol as for the 5 ml of the clear aqueous solution taken out at 2 hour. Based on the HPLC data and the measurement data of Example 19, the Docetaxel concentrations of the solution DC-5-24h have been calculated and shown in the Table 6. At 24 hour, the Docetaxel concentration of the clear aqueous solution after the filtration was about 96.05% of the Docetaxel concentration of the clear aqueous solution at 0 hour before the filtration.

TABLE 6

| Solution Number | Docetaxel Concentration (mg/ml) | Average Docetaxel Concentration (mg/ml) |
|---|---|---|
| DC-5-24h-1 | 0.4710 | 0.4714 |
| DC-5-24h-2 | 0.4720 | |
| DC-5-24h-3 | 0.4712 | |

At 48 hour, 5 ml of the clear aqueous solution was taken out from the remaining 19 ml of the aqueous solution. The experiments were done for the 5 ml of the clear aqueous solution taken out at 24 hour using the same protocol as for the 5 ml of the clear aqueous solution taken out at 2 hour. Based on the HPLC data and the measurement data of Example 19, the Docetaxel concentrations of the solution DC-5-48h have been calculated and shown in the Table 7. At 48 hour, the Docetaxel concentration of the clear aqueous solution after the filtration was about 89.10% of the Docetaxel concentration of the clear aqueous solution at 0 hour before the filtration.

TABLE 7

| Solution Number | Docetaxel Concentration (mg/ml) | Average Docetaxel Concentration (mg/ml) |
|---|---|---|
| DC-5-48h-1 | 0.4370 | 0.4373 |
| DC-5-48h-2 | 0.4380 | |
| DC-5-48h-3 | 0.4370 | |

At 72 hour, 5 ml of the clear aqueous solution was taken out from the remaining 14 ml of the aqueous solution. The experiments were done for the 5 ml of the clear aqueous solution taken out at 24 hour using the same protocol as for the 5 ml of the clear aqueous solution taken out at 2 hour. Based on the HPLC data and the measurement data of Example 19, the Docetaxel concentrations of the solution DC-5-72h have been calculated and shown in the Table 8. At 72 hour, the Docetaxel concentration of the clear aqueous solution after the filtration was about 75.57% of the Docetaxel concentration of the clear aqueous solution at 0 hour before the filtration.

TABLE 8

| Solution Number | Docetaxel Concentration (mg/ml) | Average Docetaxel Concentration (mg/ml) |
|---|---|---|
| DC-5-72h-1 | 0.3707 | 0.3708 |
| DC-5-72h-2 | 0.3703 | |
| DC-5-72h-3 | 0.3713 | |

Example 21: Pharmacokinetics Study of Composition Comprising Docetaxel and Human Serum Albumin (HSA)

A group of 3 Sprague Dawley® ("SD") male rats were used in pharmacokinetics study. The dosing route of the study was IV. The dose for the PK study of the composition comprising Docetaxel and HSA (the ratio by weight of Docetaxel to HSA in the composition is about 1:85) was 680 mg/kg. The 11 time points for the study were 0.083, 0.25, 0.5, 1, 2, 4, 8, 12, 24, 36 and 48 hr post dose. All blood samples were collected from carotid artery cannula. Blood samples were transferred into EDTA-K2 anti-coagulant tube and immediately placed on ice. Blood samples will be processed for plasma by centrifugation at approximately 4° C., 3000 g within half an hour of collection. Plasma samples will be stored in polypropylene tubes, quick frozen over dry ice and kept at −70±10° C. until LC/MS/MS analysis.

An LC-MS/MS method was developed for Docetaxel in male SD rat plasma. Table 9 shows the PK parameters of the PK study. FIG. 1 shows mean plasma concentration-time data for Docetaxel after an IV dose of 680 mg/kg of the composition comprising Docetaxel and HSA in SD rats.

TABLE 9

| CL (mL/min/kg) | Vdss (L/kg) | $T_{1/2}$ (hr) | $AUC_{0-last}$ (ng · h/mL) |
|---|---|---|---|
| 140 | 112 | 15.8 | 600 |

Example 22: Composition Comprising Docetaxel and Human Serum Albumin (HSA)

The Ratio by Weight of Docetaxel to HSA Prepared was about 1:100.

Docetaxel (100 mg) was dissolved in methanol (42.9 ml) in a glass vial to give a clear solution. HSA (10 g) (native fatty acid free human serum albumin purchased from Sera-Care Life Sciences, product code: HS-455-80, which contains fatty acids <0.2 mg/gm) as a powder was dissolved in 100 ml of water in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 23: Composition Comprising Docetaxel and Human Serum Albumin (HSA) the Ratio by Weight of Docetaxel to HSA Prepared was about 1:180

Docetaxel (10 mg) was dissolved in methanol (15.4 ml) in a glass vial to give a clear solution. A solution of HSA (1800 mg, 9 ml) (20% human serum albumin solution for infusion (product name: AlbuRx) from CSL Behring) was added into 27 ml of water to give a HSA solution (36 ml) in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 24: Composition Comprising Docetaxel and Human Serum Albumin (HSA)

The Ratio by Weight of Docetaxel to HSA Prepared was about 1:100.

Docetaxel (10 mg) was dissolved in methanol (8.6 ml) in a glass vial to give a clear solution. HSA (1000 mg) (native fatty acid free human serum albumin purchased from Golden West Biologicals, Inc., CAT #: HA1020) as a powder was dissolved in 20 ml of water in a round bottom flask. The methanol solution of Docetaxel was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 25: Measure pH Value of the Clear Aqueous Solution of Composition Comprising Docetaxel and Human Serum Albumin (HSA)

250 mg of the lyophilized solid of the composition comprising Docetaxel and HSA (the ratio by weight about 1:100) from Example 22 was dissolved in 10 ml of water to give a clear aqueous solution. The clear aqueous solution was kept at about 25° C. and measured for pH value. The pH value of the clear aqueous solution is 6.72 (3 measurements: 6.71, 6.72, and 6.72).

500 mg of the lyophilized solid of the composition comprising Docetaxel and HSA (the ratio by weight about 1:100) from Example 22 was dissolved in 10 ml of water to give a clear aqueous solution. The clear aqueous solution was kept at about 25° C. and measured for pH value. The pH value of the clear aqueous solution is 6.73 (3 measurements: 6.73, 6.74, and 6.73).

750 mg of the lyophilized solid of the composition comprising Docetaxel and HSA (the ratio by weight about 1:100) from Example 22 was dissolved in 10 ml of water to give a clear aqueous solution. The clear aqueous solution was kept at about 25° C. and measured for pH value. The pH value of the clear aqueous solution is 6.75 (3 measurements: 6.75, 6.75, and 6.76).

250 mg of the lyophilized solid of the composition comprising Docetaxel and HSA (the ratio by weight about 1:100) from Example 22 was dissolved in 10 ml of 0.9% saline solution, which had pH value about 5.41, to give a clear aqueous solution. The clear aqueous solution was kept at about 25° C. and measured for pH value. The pH value of the clear aqueous solution is 6.74 (3 measurements: 6.73, 6.74, and 6.74).

500 mg of the lyophilized solid of the composition comprising Docetaxel and HSA (the ratio by weight about 1:100) from Example 22 was dissolved in 10 ml of 0.9% saline solution, which had pH value about 5.41, to give a clear aqueous solution. The clear aqueous solution was kept at about 25° C. and measured for pH value. The pH value of the clear aqueous solution is 6.75 (3 measurements: 6.74, 6.75, and 6.76).

750 mg of the lyophilized solid of the composition comprising Docetaxel and HSA (the ratio by weight about 1:100) from Example 22 was dissolved in 10 ml of 0.9% saline solution, which had pH value about 5.41, to give a clear aqueous solution. The clear aqueous solution was kept at about 25° C. and measured for pH value. The pH value of the clear aqueous solution is 6.78 (3 measurements: 6.77, 6.79, and 6.78).

250 mg of the lyophilized solid of the composition comprising Docetaxel and HSA (the ratio by weight about 1:100) from Example 22 was dissolved in 10 ml of 5% Dextrose solution, which had pH value about 4.40, to give a clear aqueous solution. The clear aqueous solution was kept at about 25° C. and measured for pH value. The pH value of the clear aqueous solution is 6.67 (3 measurements: 6.67, 6.66, and 6.67).

500 mg of the lyophilized solid of the composition comprising Docetaxel and HSA (the ratio by weight about 1:100) from Example 22 was dissolved in 10 ml of 5% Dextrose solution, which had pH value about 4.40, to give a clear aqueous solution. The clear aqueous solution was kept at about 25° C. and measured for pH value. The pH value of the clear aqueous solution is 6.75 (3 measurements: 6.73, 6.75, and 6.76).

750 mg of the lyophilized solid of the composition comprising Docetaxel and HSA (the ratio by weight about 1:100) from Example 22 was dissolved in 10 ml of 5% Dextrose solution, which had pH value about 4.40, to give a clear aqueous solution. The clear aqueous solution was kept at about 25° C. and measured for pH value. The pH value of the clear aqueous solution is 6.76 (3 measurements: 6.75, 6.76, and 6.76).

Example 26: Measure pH Value of the Clear Aqueous Solution of Composition Comprising Docetaxel and Human Serum Albumin (HSA)

500 mg of the lyophilized solid of the composition comprising Docetaxel and HSA (the ratio by weight about 1:180) from Example 23 was dissolved in 10 ml of water to give a clear aqueous solution. The clear aqueous solution was kept at about 25° C. and measured for pH value. The pH value of the clear aqueous solution is 7.10 (3 measurements: 7.09, 7.10, and 7.11).

Example 27: Measure pH Value of the Clear Aqueous Solution of Composition Comprising Docetaxel and Human Serum Albumin (HSA)

250 mg of the lyophilized solid of the composition comprising Docetaxel and HSA (the ratio by weight about 1:100) from Example 24 was dissolved in 10 ml of water to give a clear aqueous solution. The clear aqueous solution was kept at about 25° C. and measured for pH value. The pH value of the clear aqueous solution is 6.85 (3 measurements: 6.86, 6.84, and 6.85).

Example 28: Composition Comprising Paclitaxel and Human Serum Albumin (HSA)

The Ratio by Weight of Paclitaxel to HSA Prepared was about 1:240.

Paclitaxel (2 mg) was dissolved in methanol (4.3 ml) in a glass vial to give a clear solution. HSA (480 mg) (native fatty acid free human serum albumin purchased from Sera-Care Life Sciences, product code: HS-455-80, which contains fatty acids <0.2 mg/gm) as a powder was dissolved in 10 ml of water in a round bottom flask. The methanol solution of Paclitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 29: Composition Comprising Paclitaxel and Human Serum Albumin (HSA)

The Ratio by Weight of Paclitaxel to HSA Prepared was about 1:200.

Paclitaxel (3 mg) was dissolved in methanol (5.1 ml) in a glass vial to give a clear solution. HSA (600 mg) (native fatty acid free human serum albumin purchased from Sera-Care Life Sciences, product code: HS-455-80, which contains fatty acids <0.2 mg/gm) as a powder was dissolved in 12 ml of water in a round bottom flask. The methanol solution of Paclitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid. A sample of 100 mg of the lyophilized solid was reconstituted by adding 2 mL water to give a cloudy solution.

Example 30: Composition Comprising Paclitaxel and Human Serum Albumin (HSA)

The Ratio by Weight of Paclitaxel to HSA Prepared was about 1:160.

Paclitaxel (3 mg) was dissolved in methanol (4.3 ml) in a glass vial to give a clear solution. HSA (480 mg) (native fatty acid free human serum albumin purchased from Sera-Care Life Sciences, product code: HS-455-80, which contains fatty acids <0.2 mg/gm) as a powder was dissolved in 10 ml of water in a round bottom flask. The methanol solution of Paclitaxel was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid. A sample of 100 mg of the lyophilized solid was reconstituted by adding 2 mL water to give a cloudy solution. The solution stayed cloudy and formed the white precipitations in about 2 hours.

Example 31: Composition Comprising Paclitaxel and Human Serum Albumin (HSA)

The Ratio by Weight of Paclitaxel to HSA Prepared was about 1:120.

Paclitaxel (3 mg) was dissolved in methanol (3 ml) in a glass vial to give a clear solution. HSA (360 mg) (native fatty acid free human serum albumin purchased from Sera-Care Life Sciences, product code: HS-455-80, which contains fatty acids <0.2 mg/gm) as a powder was dissolved in 7 ml of water in a round bottom flask. The methanol solution of Paclitaxel was added slowly dropwise into the flask of the HSA solution with rapid stirring at 0° C. Upon completion of the addition, a clear solution was obtained. After the methanol in the solution was removed under vacuum, a cloudy solution was obtained.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition comprising a non-covalently bound complex comprising Docetaxel and human serum albumin, wherein the molar ratio of Docetaxel and the human serum albumin in the composition is from about 0.1:1 to about 5:1, wherein the composition is a clear aqueous solution, wherein the human serum albumin in the composition is from commercial pharmaceutical human serum albumin solution for infusion, wherein the docetaxel concentration in the solution is higher than aqueous solubility of docetaxel, and wherein pH of the composition is from about 5 to about 8.

2. The composition of claim 1, wherein the molar ratio of Docetaxel and the human serum albumin is from about 0.5:1 to about 2:1.

3. The composition of claim 1, wherein the molar ratio of Docetaxel and the human serum albumin is about 1:1.

4. The composition of claim 1, wherein pH of the composition is from about 5.5 to about 7.5.

5. A method for the preparation of the composition of claim 1, said method comprising: mixing an organic solution of Docetaxel in a polar water-miscible organic solvent and a first aqueous solution containing human serum albumin to form a second aqueous solution, wherein the second aqueous solution is a clear aqueous solution.

6. The method of claim 5, further comprising removing said polar water miscible organic solvent and water from the second aqueous solution.

7. A pharmaceutical composition comprising Docetaxel and human serum albumin, wherein the Docetaxel and the human serum albumin in the composition have a ratio by weight from about 1:50 to about 1:1000, wherein the composition is a clear aqueous solution, wherein the human serum albumin in the composition is from commercial pharmaceutical human serum albumin solution for infusion, wherein the docetaxel concentration in the solution is higher than aqueous solubility of docetaxel, and wherein pH of the composition is from about 5 to about 8.

8. The composition of claim 7, wherein the Docetaxel and the human serum albumin in the composition have a ratio by weight from about 1:60 to about 1:300.

9. The composition of claim 7, wherein the Docetaxel and the human serum albumin in the composition have a ratio by weight from about 1:80 to about 1:200.

10. The composition of claim 7, wherein the composition is substantially free of solvent other than water.

11. The composition of claim 7, wherein the composition is a clear aqueous solution for at least 3 hours.

12. A method of treating a cancer, the method comprising the step of administering to a subject in need thereof a therapeutically effective amount of a pharmaceutical composition of claim 1.

13. The method of claim 12, wherein the cancer is selected from the group consisting of breast cancer, non-small cell lung cancer, prostate cancer, gastric cancer, head and neck cancer, ovarian cancer, pancreatic cancer, and Kaposi's sarcoma.

* * * * *

UNITED STATES PATENT AND TRADEMARK OFFICE
CERTIFICATE OF CORRECTION

| | | |
|---|---|---|
| PATENT NO. | : 11,419,842 B2 | Page 1 of 1 |
| APPLICATION NO. | : 16/345615 | |
| DATED | : August 23, 2022 | |
| INVENTOR(S) | : Qun Sun | |

It is certified that error appears in the above-identified patent and that said Letters Patent is hereby corrected as shown below:

On the Title Page

Column 2, item (56), Line 7, delete "Anesthesis" and insert -- Anesthesia --

Column 2, item (56), Line 26, delete "Pharmcol.," and insert -- Pharmacol., --

Signed and Sealed this
Twenty-fifth Day of June, 2024

Katherine Kelly Vidal
*Director of the United States Patent and Trademark Office*